United States Patent
Kim et al.

(10) Patent No.: US 10,329,569 B2
(45) Date of Patent: Jun. 25, 2019

(54) COMPOSITION FOR REDUCING CELLULAR SENESCENCE LEVEL INCLUDING ACTIVITY INHIBITOR INHIBITING DCUN1D3 ACTIVITY OR EXPRESSION INHIBITOR INHIBITING EXPRESSION OF DCUN1D3-ENCODING GENE AND USE THEREOF

(71) Applicant: Samsung Electronics Co., Ltd., Suwon-si, Gyeonggi-do (KR)

(72) Inventors: Myoungsoon Kim, Anyang-si (KR); Yongsub Kim, Suwon-si (KR); Young-Sam Lee, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 15/681,262

(22) Filed: Aug. 18, 2017

(65) Prior Publication Data

US 2018/0002703 A1 Jan. 4, 2018

Related U.S. Application Data

(62) Division of application No. 15/200,937, filed on Jul. 1, 2016, now abandoned.

(30) Foreign Application Priority Data

| Jul. 1, 2015 | (KR) | 10-2015-0094272 |
| Jan. 25, 2016 | (KR) | 10-2016-0008900 |

(51) Int. Cl.
*C12N 15/11* (2006.01)
*C07H 21/02* (2006.01)
(Continued)

(52) U.S. Cl.
CPC ........ *C12N 15/1138* (2013.01); *C12N 15/113* (2013.01); *C12N 2310/113* (2013.01);
(Continued)

(58) Field of Classification Search
CPC .............. C12N 15/113; C12N 15/1135; C12N 2310/531; C12N 15/1138; C12N 2310/14;
(Continued)

(56) References Cited

U.S. PATENT DOCUMENTS

| 7,927,806 B2 | 4/2011 | Busse et al. |
| 8,354,384 B2 | 1/2013 | Slack et al. |

(Continued)

FOREIGN PATENT DOCUMENTS

| KR | 2014-0166631 | 6/2016 |
| WO | WO 2009/137912 A1 | 11/2009 |
| WO | WO 2015/073531 A1 | 5/2015 |

OTHER PUBLICATIONS

Dowson JH (Br. J. Psychiatry, 1982, vol. 140:142-148).*

(Continued)

*Primary Examiner* — Terra C Gibbs
(74) *Attorney, Agent, or Firm* — Leydig, Voit & Mayer, Ltd.

(57) ABSTRACT

Provided is a composition and method for reducing a cellular senescence level by inhibiting the activity or expression of one or more of DCUN1D3 protein or gene encoding same and a polynucleotide having a nucleotide sequence of SEQ ID NO: 5, as well as a method of treating a disease or a disease symptom associated with an increased cellular senescence level in a mammal.

7 Claims, 14 Drawing Sheets

Specification includes a Sequence Listing.

(51) Int. Cl.
*C07H 21/04* (2006.01)
*C12N 15/113* (2010.01)

(52) U.S. Cl.
CPC .... *C12N 2310/14* (2013.01); *C12N 2310/141* (2013.01); *C12N 2310/20* (2017.05); *C12N 2310/531* (2013.01); *C12N 2320/30* (2013.01)

(58) Field of Classification Search
CPC .......... C12N 2310/113; C12N 2320/30; A61K 31/7105; C12Q 1/6883; C12Q 2600/158; C12Q 2600/136
See application file for complete search history.

(56) References Cited

U.S. PATENT DOCUMENTS

| | | |
|---|---|---|
| 8,476,259 B2 | 7/2013 | Fong |
| 2007/0049588 A1 | 3/2007 | Smith et al. |
| 2008/0279866 A1 | 11/2008 | Iacomini et al. |
| 2012/0010196 A1 | 1/2012 | Qin et al. |
| 2012/0052487 A9 | 3/2012 | Khvorova |
| 2012/0149645 A1 | 6/2012 | Mao |
| 2013/0183369 A1 | 7/2013 | Furber |
| 2014/0179593 A1 | 6/2014 | Monda et al. |
| 2014/0200156 A1 | 7/2014 | Kim et al. |
| 2016/0095864 A1 | 4/2016 | Park et al. |
| 2016/0113935 A1 | 4/2016 | Jung et al. |
| 2016/0145686 A1 | 5/2016 | Kim et al. |
| 2016/0362686 A1 | 12/2016 | Ryu et al. |

OTHER PUBLICATIONS

Greussing et al, "Identification of microRNA-mRNA functional interactions in UVB-induced senescence of human diploid fibroblasts," *BMC Genomics*, vol. 14, No. 1 (2013).

Huang et al., SCCRO3 (DCUN1D3) Antagonizes the Neddylation and Oncogenic Activity of SCCRO (DCUN1D1), *Journal of Biological Chemistry*, vol. 289, No. 50, pp. 34728-34742 (2014).

Ma, T. et al. (2008), DCUNID3, a novel UVC-responsive gene that is involved in cell cycle progression and cell growth. Cancer Science, 99: 2128-2135. doi: 10.1111/j.1349-7006.2008.00929.x.

Ma et al., "DCUN1 D3, a novel UVC-responsive gene that is involved in cell cycle progression and cell growth", *Cancer Sci*, 99(11): 2128-2135 (2008).

Extended European Search Report in 16177214.0 dated Nov. 18, 2016.

* cited by examiner

Control shRNA  DCUN1D3 shRNA

COMPOSITION FOR REDUCING CELLULAR SENESCENCE LEVEL INCLUDING ACTIVITY INHIBITOR INHIBITING DCUN1D3 ACTIVITY OR EXPRESSION INHIBITOR INHIBITING EXPRESSION OF DCUN1D3-ENCODING GENE AND USE THEREOF

CROSS-REFERENCE TO RELATED APPLICATIONS

This application is a divisional of U.S. patent application Ser. No. 15/200,937 filed on Jul. 1, 2016, now abandoned, which in turn claims the benefit of Korean Patent Application No. 10-2015-0094272 filed on Jul. 1, 2015, and Korean Patent Application No. 10-2016-0008900, filed on Jan. 25, 2016, in the Korean Intellectual Property Office, the entire disclosures of which are hereby incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 14,085 byte ASCII (Text) file named "730578_ST25.TXT_revised" created Aug. 17, 2017.

BACKGROUND

1. Field

The present disclosure relates to a composition for reducing a cellular senescence level, a method of reducing a cellular senescence level in a mammal, and a method of treating a disease or a disease symptom associated with an increased cellular senescence level in a mammal.

2. Description of the Related Art

Senescence may be defined as a permanent halt in cell division. Replicative senescence or cellular senescence is observed as a model for aging at a cellular level. When cells are consecutively cultured, the cells are divided a number of times, but the cells no longer divide once senescence is reached. Senescent cells often have resistance to programmed cell death, and, in some cases, the senescent cells are maintained in a non-dividing state for years.

DCUN1D3 was found during the process of high throughput screening of novel human genes associated with serum response element (SRE) pathway activation. The DCUN1D3 gene is highly conserved among vertebrates. Human DCUN1D3 complementary DNA (cDNA) encodes 304 amino acids with an apparent molecular weight of 34 kDa. An amino acid sequence of DCUN1D3 and a nucleotide sequencing encoding the same may be those described in Genbank Accession Nos. NP_775746.1 and NM_173475.2, respectively. DCUN1D3 is broadly expressed in several tumor tissues and cultured cell lines. UV irradiation significantly increases DCUN1D3 expression levels in cancer cell lines.

Under this background, there remains a demand for a composition for reducing a cellular senescence level and a method thereof.

SUMMARY

An aspect provides a composition for reducing a cellular senescence level.

Another aspect provides a method of reducing a cellular senescence level in a mammal.

Still another aspect provides a method of treating a disease or a disease symptom associated with an increased cellular senescence level in a mammal.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
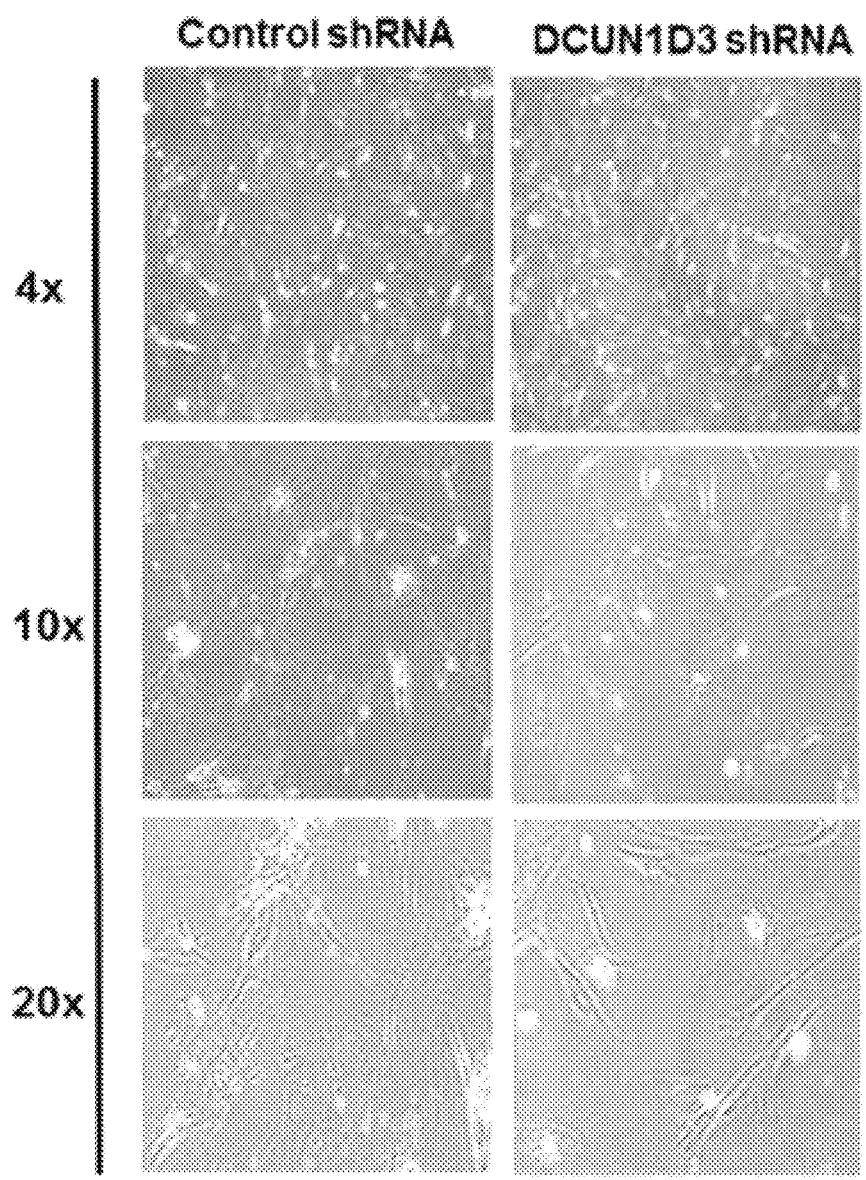
FIG. 1 is a microscopic image of cultured senescent cells transfected with DCUN1D3 shRNA-containing lentivirus.

Provided herein is a composition for reducing a cellular senescence level, the composition including an activity inhibitor inhibiting activity of one or more of DCN1, defective in cullin neddylation 1, domain containing 3 (DCUN1D3) protein and a polynucleotide having a nucleotide sequence of SEQ ID NO: 5, or an expression inhibitor inhibiting expression of one or more of a gene encoding DCUN1D3 and a gene encoding the nucleotide sequence of SEQ ID NO: 5 as an active ingredient.

DCUN1D3 was found during the process of high throughput screening of novel human genes associated with serum response element (SRE) pathway activation. The DCUN1D3 gene is highly conserved among vertebrates. Human DCUN1D3 complementary DNA (cDNA) encodes 304 amino acids with an apparent molecular weight of 34 kDa. An amino acid sequence of DCUN1D3 and a nucleotide sequence encoding the same may be those described in Genbank Accession Nos. NP_775746.1 (SEQ ID NO: 3) and NM_173475.2 (SEQ ID NO: 4). DCUN1D3 is broadly expressed in several tumor tissues and cultured cell lines. UV irradiation significantly increases a DCUN1D3 expression level in cancer cell lines.

The activity inhibitor inhibiting DCUN1D3 activity may be a substance inhibiting neddylation activity of DCUN1D3. Neddylation may be a process by which the ubiquitin-like protein NEDD8 is conjugated to its target protein.

The nucleic acid with the nucleotide sequence of SEQ ID NO: 5 (hereinafter, referred to as "SEAT1 (senescence-associated transcript 1) RNA" gene) may be a gene encoding a long non-coding ribonucleic acid (lncRNA). The non-coding RNA is a functional RNA molecule which is not translated into a protein. The ncRNA may be small nucleolar RNA (snoRNA), microRNA, small interfering RNA (siRNA), small nuclear RNA (snRNA), extracellular RNA (exRNA), Piwi-interacting RNA (piRNA), or long ncRNA (lncRNA). The lncRNA is a transcript, which is not translated into a protein or has a low protein-coding potential, and has a length of about 50 nucleotides or more, about 100 nucleotides or more, about 200 nucleotides or more, or about 500 nucleotides or more. The nucleic acid of the nucleotide sequence of SEQ ID NO: 5 may be a nucleic acid from a nucleic acid located at p-arm of human chromosome 16. The nucleic acid of the nucleotide sequence of SEQ ID NO: 5 may be a nucleic acid from a nucleic acid located between an ERI1 Exoribonuclease Family Member 2 (ERI2) gene of human chromosome 16 and a DCN1, Defective In Cullin Neddylation 1, Domain Containing 3 (DCUN1D3) gene. The nucleic acid of the nucleotide sequence of SEQ ID NO: 5 may have a sequence of GenBank Accession No. AK027199.

An activity inhibitor inhibiting SEAT1 RNA activity may be small interference RNA (siRNA) against SEAT1 RNA, small hairpin RNA (shRNA), antisense oligonucleotide, miRNA, or a combination thereof. The siRNA be short double-stranded RNA(dsRNA) with phosphorylated 5' ends and hydroxylated 3' ends with two overhaning nucleotides. The siRNA may have 20 to 24 nucleotides in length. The siRNA may have a complementary nucleotide sequence to the mRNA of the target gene. The siRNA against SEAT1 RNA may include a polynucleotide of SEQ ID NO: 6 and a polynucleotide of SEQ ID NO: 7 (SEAT1 siRNA #1); a polynucleotide of SEQ ID NO: 8 and a polynucleotide of SEQ ID NO: 9 (SEAT1 siRNA #2); or a polynucleotide of SEQ ID NO: 10 and a polynucleotide of SEQ ID NO: 11 (SEAT1 siRNA #3). The activity inhibitor inhibiting SEAT1 RNA activity may be also an expression inhibitor inhibiting DCUN1D3 expression.

The gene encoding SEAT1 RNA may be located at p-arm of human chromosome 16. The gene may be AK027199 gene, namely, a polynucleotide of SEQ ID NO: 5. The gene encoding SEAT1 RNA may be located between ER12 gene of human chromosome 16 and DCUN1D3 gene.

The expression inhibitor inhibiting expression of genes encoding one or more of DCUN1D3 and SEAT1 RNA may be any expression inhibitor, as long as it reduces expression of genes encoding one or more of DCUN1D3 and SEAT1 RNA in cells. The expression inhibitor may be siRNA, shRNA, miRNA, antisense oligonucleotide, or a combination thereof. The siRNA against the DCUN1D3 gene may include a nucleotide sequence of SEQ ID NO: 1 and a nucleotide sequence of SEQ ID NO: 2 (DCUN1D3 siRNA #1). The siRNA against SEAT1 RNA may include a polynucleotide of SEQ ID NO: 6 and a polynucleotide of SEQ ID NO: 7 (SEAT1 siRNA #1); a polynucleotide of SEQ ID NO: 8 and a polynucleotide of SEQ ID NO: 9 (SEAT1 siRNA #2); or a polynucleotide of SEQ ID NO: 10 and a polynucleotide of SEQ ID NO: 11 (SEAT1 siRNA #3). The expression inhibitor inhibiting expression of the SEAT1 RNA-encoding gene may be also an expression inhibitor inhibiting expression of DCUN1D3-encoding gene.

The expression inhibitor inhibiting expression of the DCUN1D3-encoding gene may be any expression inhibitor, as long as it reduces expression of the DCUN1D3 gene in cells. The expression inhibitor may be small interference RNA (siRNA), small hairpin RNA (shRNA), antisense oligonucleotide, or a combination thereof. The siRNA may include a nucleotide sequence of SEQ ID NO: 1 and a nucleotide sequence of SEQ ID NO: 2. The expression inhibitor may be miR-20b.

In the composition, a reduction in the cellular senescence level may refer to delay or prevention of cellular senescence, or reversion of a senescent cell to a younger cell state (e.g., non-senescent cell).

In the composition, the reduction in the cellular senescence level may include one or more of an increase in proliferation of a cell, an increase in activity of autophagy, a reduction in accumulation of lipofuscin, a reduction in activity of 3-galactosidase, a reduction in the number of mitochondrial reactive oxygen species, and an increase in mitochondrial membrane potential. The cell may be a muscle cell including myoblast, fibroblast, early senescent cell, or nerve cell. The early senescent cell may be a cell derived (obtained) from a patient with progeria. Progeria may be Hutchinson-Gilford progeria or Werner syndrome.

The composition may be used to treat a disease or a disease symptom associated with increased cellular senescence level. The disease or disease symptom associated with increased cellular senescence level may include skin wrinkles, wound healing declines, sarcopenia, muscular dystrophy, early senescent symptom (e.g., Hutchinson-Gilford progeria syndrome), or a combination thereof. The disease or disease symptom associated with increased cellular senescence level may include a disease or a disease symptom associated with lipofuscin accumulation. The disease or disease symptom associated with lipofuscin accumulation may be neuronal ceroid lipofuscinoses (NCL), age-related macular degeneration, neurofibrillary tangles, brown atrophy of the heart, Alzheimer's disease, Parkinson's disease, amyotrophic lateral sclerosis (ALS), acromegaly, denervation atrophy, lipid myopathy, or chronic obstructive pulmonary disease (COPD). In addition, the disease or disease symptom associated with increased cellular senescence level may be a disease caused by mitochondrial damage such as an increase in mitochondrial ROS, reduction in mitochondrial membrane potential, or a combination thereof. In addition, the disease or disease symptom associated with increased cellular senescence level may be a disease caused by increased activity of β-galactosidase in a cell.

The activity inhibitor inhibiting activity of one or more of the DCUN1D3 protein and the polynucleotide having the nucleotide sequence of SEQ ID NO: 5, or the expression inhibitor inhibiting expression of one or more of the gene encoding DCUN1D3 and the gene encoding the nucleotide sequence of SEQ ID NO: 5 may be prepared as a pharmaceutically acceptable salt.

The cells may be cells of a mammal including a human. The mammal may have a disease associated with increased cellular senescence level. The cells may exist in vitro or in vivo. The cells may be fibroblasts or nerve cells.

The composition may further include a pharmaceutically acceptable carrier. In the composition, the "pharmaceutically acceptable carrier" generally refers to an inert material, i.e., a material used in combination with an active ingredient to assist the application of the active ingredient. The carrier may include a pharmaceutically acceptable excipient, additive, or diluent generally used. The carrier may include one or more selected from, for example, a filler, a binder, a disintegrant, a buffer, a preservative, an antioxidant, a lubricant, a flavoring agent, a thickener, a coloring agent, an emulsifier, a suspending agent, a stabilizer, and an isotonic agent.

The carrier may include a vehicle for delivering nucleotide to a subject for example, a mammal. The vehicle may include nanoparticle, DNA templates encoding siRNA sequences, cationic liposomes, cholesterol conjugates, antibody conjugates cationic lipids, such as Lipofectamine, a positively charged peptide or protein, and/or peptide-mediated delivery systems. A number of approaches for delivering siRNA to a specific target cell's cytoplasm may be used, ranging in complexity from simple naked siRNAs to complicated nanoparticle-based delivery vehicles. Examples include, but are not limited to, DNA templates encoding siRNA sequences may be delivered to cells that can be transcribed to express siRNAs; the use of cationic liposomes, cholesterol conjugates, antibody conjugates, electroporation, direct injection, hydrodynamic transfection, electrical pulsing or any other suitable method of direct delivery; cationic lipids, such as Lipofectamine, as a transfection reagent may be used to deliver siRNA in vitro; siRNA may be delivered systemically using cholesterol conjugates, liposomes, and polymer-based nanoparticle sized delivery vehicles; and siRNA may be delivered via peptide-mediated delivery systems. Plasmid or viral vectors for the delivery may be used.

According to some embodiments, a positively charged peptide or protein may be used to produce a protein-siRNA complex that can be used to deliver siRNAs. The phosphate backbone of siRNAs is negatively charged and allows complex formation with cationic peptides and proteins regardless of its sequence. In some embodiments, the protein-siRNA complex can include a non-specific cell-penetrating peptide (e.g. Tat) to deliver the to cells. In other embodiments, the protein-siRNA complex can include a targeting moiety, such as a receptor-binding peptide or antibody for specific delivery. The composition may include the activity inhibitor inhibiting activity of one or more of the DCUN1D3 protein and the polynucleotide having the nucleotide sequence of SEQ ID NO: 5, or the expression inhibitor inhibiting expression of one or more of the gene encoding DCUN1D3 and the gene encoding the nucleotide sequence of SEQ ID NO: 5, the pharmaceutically acceptable salt thereof, or the solvate in a "therapeutically effective amount". In the composition, the "therapeutically effective amount" refers to an amount that is sufficient enough to indicate a therapeutic effect when administered to a subject in need of treatment. The term "treatment" refers to a practice of treating a disease or a medical symptom, e.g., a disease associated with cellular senescence, in a subject such as a mammal including a human, and examples of the treatment are as follows: (a) prevention of the occurrence of a disease or a medical symptom, that is, prophylactic treatment of a patient; (b) alleviation of a disease or a medical symptom, that is, involvement of removal or recovery of a disease or a medical symptom in a patient; (c) inhibition of a disease or a medical symptom, that is, involvement of delaying or stopping a disease or a medical symptom in a subject; or (d) reduction of a disease or a medical symptom in a subject. The "effective amount" may be appropriately selected by one of ordinary skill in the art. For example, the "effective amount" may be in a range from about 0.01 mg to about 10,000 mg, about 0.1 mg to about 1,000 mg, about 1 mg to about 100 mg, about 0.01 mg to about 1,000 mg, about 0.01 mg to about 100 mg, about 0.01 mg to about 10 mg, or about 0.01 mg to about 1 mg per day.

The composition may be administered orally to a subject, or parenterally to a subject in a way of intravenous, intraperitoneal, subcutaneous, rectal, and topical administration. Therefore, the composition may be formulated in various forms including tablets, capsules, aqueous solutions, or suspensions. In the case of tablet formulation for oral use, an excipient such as lactose or corn starch, and a lubricant such as magnesium stearate, may be generally added to the composition. In the case of capsule formulation for oral use, lactose and/or dry corn starch may be used as a diluent. When an aqueous suspension for oral use is required, an active ingredient may be used in combination with an emulsifier and/or a suspending agent. If necessary, a particular sweetening agent and/or a flavoring agent may be added. In the case of neural, intramuscular, intraperitoneal, subcutaneous, and intravenous administration, a sterile solution of an active ingredient is generally prepared, thereby appropriately adjusting and buffering the pH of the solution. In the case of intravenous administration, the total concentration of solutes is adjusted to render the formulation isotonicity. The composition may be prepared as an aqueous solution containing a pharmaceutically acceptable carrier having a pH of 7.4 as of salt water. The aqueous solution may be introduced into muscle or nerve blood flow of a patient by local bolus injection.

The term "cellular senescence (or senescence of a cell)" as used herein refers to, as compared with a reference cell, one or more of reduction in proliferation of a cell, reduction in activity of autophagy, accumulation of lipofuscin, increase in β-galactosidase activity, increase in the number of mitochondrial ROS, and reduction in mitochondrial membrane potential, or to a process causing the phenomena above. Herein, the reference cell may be a known non-senescent cell of the same type. The term "young cell" refers to, as compared with a reference cell, a cell with one or more of increased proliferation of a cell, increased activity of autophagy, decreased accumulation of lipofuscin, decreased activity of β-galactosidase, decreased number of mitochondrial ROS, and increased mitochondrial membrane potential. Herein, the reference cell may be a known senescent cell of the same type. A non-senescent cell as the reference cell may be a cell, for example, a fibroblast or a nerve cell derived from a person aged about 18 to about 25, about 18 to about 23, or about 18 to about 20 who are normal and healthy.

The composition may be used in combination with one or more additional therapeutic agents to treat a disease associated with increased cellular senescence level. Alternatively, the composition may be free of other active ingredients to treat a disease associated with increased cellular senescence level other than the activity inhibitor inhibiting activity of one or more of the DCUN1D3 protein and the polynucleotide having the nucleotide sequence of SEQ ID NO: 5, or the expression inhibitor inhibiting expression of one or more of the gene encoding DCUN1D3 and the gene encoding the nucleotide sequence of SEQ ID NO: 5, the pharmaceutically acceptable salt thereof, or the solvate thereof.

Another aspect provides a composition for reducing accumulation of lipofuscin in cells, the composition including the activity inhibitor inhibiting activity of one or more of the DCUN1D3 protein and the polynucleotide having the nucleotide sequence of SEQ ID NO: 5, or the expression inhibitor inhibiting expression of one or more of the gene encoding DCUN1D3 and the gene encoding the nucleotide sequence of SEQ ID NO: 5 as an active ingredient. The composition may be used to treat a disease or a disease symptom associated with accumulation of lipofuscin in cells. The disease or disease symptom associated with accumulation of lipofuscin may be NCL, age-related macular degeneration, neurofibrillary tangles, brown atrophy of the heart, Alzheimer's disease, Parkinson's disease, ALS, acromegaly, denervation atrophy, lipid myopathy, or COPD. The terms used in the 'composition for reducing accumulation of lipofuscin in cells' are the same as those in the 'composition for reducing a cellular senescence level', unless otherwise mentioned herein.

Still another aspect provides a composition for increasing proliferation of a cell, the composition including the activity inhibitor inhibiting activity of one or more of the DCUN1D3 protein and the polynucleotide having the nucleotide sequence of SEQ ID NO: 5, or the expression inhibitor inhibiting expression of one or more of the gene encoding DCUN1D3 and the gene encoding the nucleotide sequence of SEQ ID NO: 5 as an active ingredient. The composition may be used to treat a disease or a disease symptom associated with reduced proliferation of a cell. The disease or disease symptom associated with reduced proliferation of a cell may be skin wrinkles, wound healing declines, sarcopenia, muscular dystrophy, early senescent symptom (e.g., Hutchinson-Gilford progeria syndrome), or a combination thereof. The terms used in the 'composition for increasing proliferation of a cell' are the same as those in the 'composition for reducing a cellular senescence level', unless otherwise mentioned herein.

Still another aspect provides a method of reducing a cellular senescence level in a mammal, the method including administering an effective amount of the activity inhibitor inhibiting activity of one or more of the DCUN1D3 protein and the polynucleotide having the nucleotide sequence of SEQ ID NO: 5, or the expression inhibitor inhibiting expression of one or more of the gene encoding DCUN1D3 and the gene encoding the nucleotide sequence of SEQ ID NO: 5 to the mammal to reduce a cellular senescence level.

The "activity inhibitor inhibiting activity of one or more of the DCUN1D3 protein and the polynucleotide having the nucleotide sequence of SEQ ID NO: 5, or the expression inhibitor inhibiting expression of one or more of the gene encoding DCUN1D3 and the gene encoding the nucleotide sequence of SEQ ID NO: 5, "reducing cellular senescence level" and "mammal" used regarding the method are the same as described above. The effective amount refers to "an amount sufficient enough to reduce a cellular senescence level" when administered to a subject. The administration refers to administration of the above-described composition including "the activity inhibitor inhibiting activity of one or more of the DCUN1D3 protein and the polynucleotide having the nucleotide sequence of SEQ ID NO: 5, or the expression inhibitor inhibiting expression of one or more of the gene encoding DCUN1D3 and the gene encoding the nucleotide sequence of SEQ ID NO: 5, the pharmaceutically acceptable salt thereof, or the solvate thereof".

Still another aspect provides a method of treating a disease or a disease symptom associated with increased cellular senescence level in a mammal, the method including administering a therapeutically effective amount of the activity inhibitor inhibiting activity of one or more of the DCUN1D3 protein and the polynucleotide having the nucleotide sequence of SEQ ID NO: 5, or the expression inhibitor inhibiting expression of one or more of the gene encoding DCUN1D3 and the gene encoding the nucleotide sequence of SEQ ID NO: 5 to a mammal to treat the disease or disease symptom associated with increased cellular senescence level.

The "activity inhibitor inhibiting activity of one or more of the DCUN1D3 protein and the polynucleotide having the nucleotide sequence of SEQ ID NO: 5, or the expression inhibitor inhibiting expression of one or more of the gene encoding DCUN1D3 and the gene encoding the nucleotide sequence of SEQ ID NO: 5, "disease or disease symptom associated with increased cellular senescence level", and "mammal" used regarding the method are the same as described above. The effective amount refers to "an amount sufficient enough to treat the disease or disease symptom associated with increased cellular senescence level" when administered to a subject having the disease or disease symptom associated with increased cellular senescence level. The administration refers to administration of the above-described composition including "the activity inhibitor inhibiting activity of one or more of the DCUN1D3 protein and the polynucleotide having the nucleotide sequence of SEQ ID NO: 5, or the expression inhibitor inhibiting expression of one or more of the gene encoding DCUN1D3 and the gene encoding the nucleotide sequence of SEQ ID NO: 5, the pharmaceutically acceptable salt thereof, or the solvate thereof".

In regard to the method, those skilled in the art may appropriately select a route of administration depending on a patient's condition. The administration may be oral, parenteral, or topical administration. The administration may be topically applied to tissue consisting of or including senescent cells. The administration may be topically applied to skin tissue, muscle tissue, or nerve tissue.

In regard to the method, the "therapeutically effective amount" is an amount that is effective enough to treat the disease or disease symptom associated with increased cellular senescence level in a mammal. The administration amount may vary, as described above, according to a variety of factors, such as a patient's condition, an administration route, or physician's determination. The effective administration amount may be estimated by a dose-response curve obtained in vitro or from an animal model test. The ratio or concentration of the compound of the present invention may be determined according to chemical properties, the route of administration, or therapeutic amounts. The administration amount may be effective in a subject when administered in a range from about 1 µg/kg to about 1 g/kg per day, or about 0.1 mg/kg to about 500 mg/kg weight per day. The administration amount may vary according to a subject's age, weight, susceptibility, or symptoms.

Still another aspect provides a method of reducing a lipofuscin level in a mammalian cell, the method including administering a therapeutically effective amount of the activity inhibitor inhibiting activity of one or more of the DCUN1D3 protein and the polynucleotide having the nucleotide sequence of SEQ ID NO: 5, or the expression inhibitor inhibiting expression of one or more of the gene encoding DCUN1D3 and the gene encoding the nucleotide sequence of SEQ ID NO: 5 to a mammal to reduce the lipofuscin level in the cell. The method may be used to treat a disease or a disease symptom associated with increased lipofuscin level in a mammalian cell. The disease or disease symptom associated with increased lipofuscin level may be NCL, age-related macular degeneration, neurofibrillary tangles, brown atrophy of the heart, Alzheimer's disease, Parkinson's disease, ALS, acromegaly, denervation atrophy, lipid myopathy, or COPD. The terms used in the 'method of reducing a lipofuscin level in a mammalian cell' are the same as those in the 'method of treating a disease or a disease symptom associated with increased cellular senescence level in a mammal', unless otherwise mentioned herein.

Still another aspect provides a method of increasing proliferation of a mammalian cell, the method including administering an effective amount of the activity inhibitor inhibiting activity of one or more of the DCUN1D3 protein and the polynucleotide having the nucleotide sequence of SEQ ID NO: 5, or the expression inhibitor inhibiting expression of one or more of the gene encoding DCUN1D3 and the gene encoding the nucleotide sequence of SEQ ID NO: 5 to a mammal to increase proliferation of the cell. The method may be used to treat a disease or a disease symptom associated with decreased proliferation of a mammalian cell. The disease or disease symptom associated with decreased proliferation of a cell may be skin wrinkles, wound healing declines, sarcopenia, muscular dystrophy, early senescent symptom (e.g., Hutchinson-Gilford progeria syndrome), or a combination thereof. The terms used in the 'method of increasing proliferation of a mammalian cell' are the same as those in the 'method of treating a disease or a disease symptom associated with increased cellular senescence level in a mammal', unless otherwise mentioned herein.

The composition according to an aspect may be used to reduce a cellular senescence level, the composition including the activity inhibitor inhibiting activity of one or more of the DCUN1D3 protein and the polynucleotide having the nucleotide sequence of SEQ ID NO: 5, or the expression inhibitor inhibiting expression of one or more of the gene encoding DCUN1D3 and the gene encoding the nucleotide sequence of SEQ ID NO: 5, the pharmaceutically acceptable salt thereof, or the solvate thereof.

The method of reducing a cellular senescence level in a mammal according to another aspect may be used to efficiently reduce the cellular senescence in the mammal.

The method of treating a disease or a disease symptom associated with increased cellular senescence level in a mammal according to still another aspect may be used to efficiently treat the disease or disease symptom associated with increased cellular senescence level in the mammal.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects. As used herein, the term "and/or" includes any and all combinations of one or more of the associated listed items.

Hereinafter, the present invention will be described in further detail with reference to the following examples. However, these examples are for illustrative purposes only and are not intended to limit the scope of the present invention.

Example 1: Influence of DCUN1D3 shRNA or siRNA on Senescent Cells (1) Induction of Proliferation of Senescent Cell DCUN1D3 shRNA was transduced into senescent cells to examine its effect on proliferation of senescent cells. Senescent cells to be used were prepared by subculturing human dermal fibroblast (HDF) M4 cells obtained from a 4-year-old boy (derived from the foreskin of a 4-year-old donor, Seoul National University) in DMEM (hereinafter, referred to as DMEM') (HyClone, Logan, Utah, USA: Cat no. SH30243) containing high concentration of glucose, glutamine, and pyruvate and being supplemented with 10% (v/v) fetal bovine serum (FBS), and 1× penicillin/streptomycin (100 U/ml penicillin, 100 ug/ml streptomycin) under conditions of 37° C. and 5% $CO_2$. The used senescent cells were at passage 33 and the cell doubling time was about 14 days or longer.

DCUN1D3 shRNA was introduced into lentivirus to prepare a DCUN1D3 shRNA-containing lentivirus, which was transduced into the senescent cells. The DCUN1D3 shRNA-containing lentiviral pLKO.1 puro vector (OriGene, USA) was prepared by synthesizing nucleotide sequences of SEQ ID NOS: 1 and 2, respectively to prepare a double stranded shRNA construct (IDT, Korea), and ligating the shRNA construct into pLKO.1 puro vector digested with restriction enzymes AgeI and EcoRI. The prepared DCUN1D3 shRNA-containing lentivirus was transduced into 293FT human embryonic kidney cells (#R700-07: Invitrogen) using Lipofectamine 2000, together with packaging vectors, VSV-G and PAX2 (OriGene, USA). Herein, during the transduction, 6 ug/ml polybrene was added to the growth medium for kidney cells to increase the transduction efficiency. On day 2 after transduction, a lentiviral supernatant was collected and concentrated using Lenti-X (Clontech, cat. no.631231).

The DCUN1D3 shRNA-containing lentivirus thus prepared was transfected into the senescent cells and subcultured in DMEM (hereinafter, referred to as DMEM') (HyClone, cat. no. SH30243, USA) containing high concentration of glucose, glutamine, and pyruvate and being supplemented with 10% (v/v) fetal bovine serum (FBS), and 1× penicillin/streptomycin (100 U/ml penicillin, 100 ug/ml streptomycin) for 4 weeks under conditions of 37° C. and 5% $CO_2$. The nucleotide sequence of the DCUN1D3 shRNA was a nucleotide sequence of SEQ ID NO: 1 (sense) and SEQ ID NO: 2 (antisense). Scrambled RNA (Bioneer, Korea) provided by the manufacturer was used as a control group.

```
SEQ ID NO: 1 (sense):
GUCACUGCAUCGGGAAAUA(dTdT)

SEQ ID NO: 2 (antisense):
UAUUUCCCGAUGCAGUGAC(dTdT)
```

FIG. 1 is a microscopic image of the cultured senescent cells transfected with DCUN1D3 shRNA-containing lentivirus. In FIG. 1, "control shRNA" indicates senescent cells transfected with scrambled shRNA-containing lentivirus, and "DCUN1D3 shRNA" indicates senescent cells transfected with DCUN1D3 shRNA-containing lentivirus. As shown in FIG. 1, the senescent cells transfected with DCUN1D3 shRNA-containing lentivirus showed an increase in the number of cells and similar morphology to young cells, compared to senescent cells transfected with scrambled shRNA-containing lentivirus, that is, a negative control group, indicating that DCUN1D3 shRNA induces proliferation of senescent cells, after introduced into the senescent cells.

(2) Reduction in Activity of Senescence-Associated Beta-Galactosidase (SA β-Gal)

Senescent cells were stained blue with X-gal due to increased activity of SA β-gal. As explained in (1), senescent cells were transfected with DCUN1D3 shRNA or scrambled shRNA-containing lentivirus, and SA β-gal activity in the cultured senescent cells was measured. Senescent cells that were transfected with none of DCUN1D3 shRNA or scrambled shRNA-containing lentivirus were used as a negative control group.

Figure 2A:
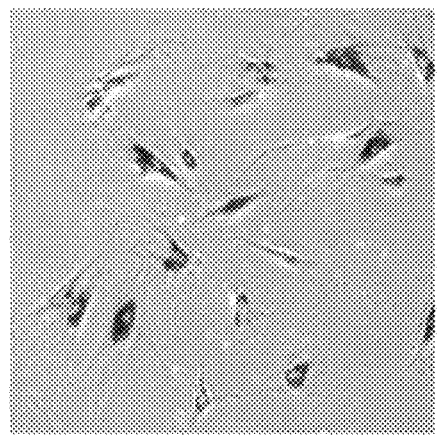
FIG. 2A is an X-gal staining image of senescent cells transfected with DCUN1D3 shRNA-containing lentivirus (panel A) or scrambled shRNA-containing lentivirus (panel B)
Figure 2A:
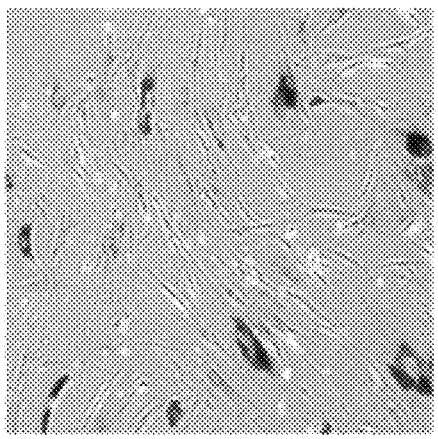

In detail, the cultured senescent cells were stained using a cellular senescence assay kit (Cell BIOLABS, INC.) according to the manufacturer's instructions, and the number of cells stained blue was counted under a microscope. FIG. 2A is an X-gal staining image (A) of senescent cells transfected with DCUN1D3 shRNA (right) or scrambled shRNA-containing lentivirus (left) and FIG. 2B is a percentage (B) of the cells stained blue in the X-gal staining image of FIG. 2A.

Figure 2B:
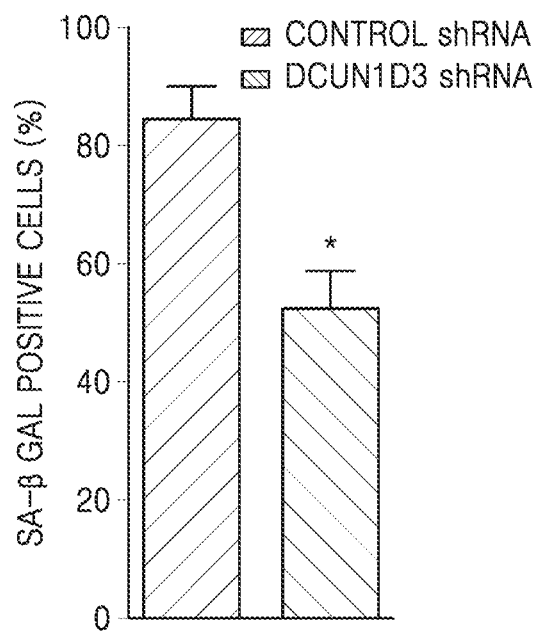
FIG. 2B is a percentage of the cells stained blue in the X-gal staining image of FIG. 2A.

As shown in FIG. 2B, about 84% of the senescent cells transfected with scrambled shRNA-containing lentivirus were stained, whereas about 52% of the senescent cells transfected with DCUN1D3 shRNA-containing lentivirus were stained. Therefore it is confirmed that SA β-gal activity was reduced by transfection of senescent cells with DCUN1D3 shRNA-containing lentivirus, indicating that a cellular senescence level is reduced by transfection of senescent cells with DCUN1D3 shRNA-containing lentivirus.

(3) Reduction in Autophagy Activity and Reduction in Lipofuscin Accumulation

It is known that senescent cells show a reduction in autophagy activity, accumulation of lipofuscin, and mitochondrial damage. In order to examine this, as described in (1), senescent cells were transfected with DCUN1D3 shRNA or scrambled shRNA-containing lentivirus, and the amount of lipofuscin was measured in the cultured senescent cells. Senescent cells that were transfected with none of DCUN1D3 shRNA or scrambled shRNA-containing lentivirus were used as a negative control group. Further, the size of the cell was measured.

Figure 3:
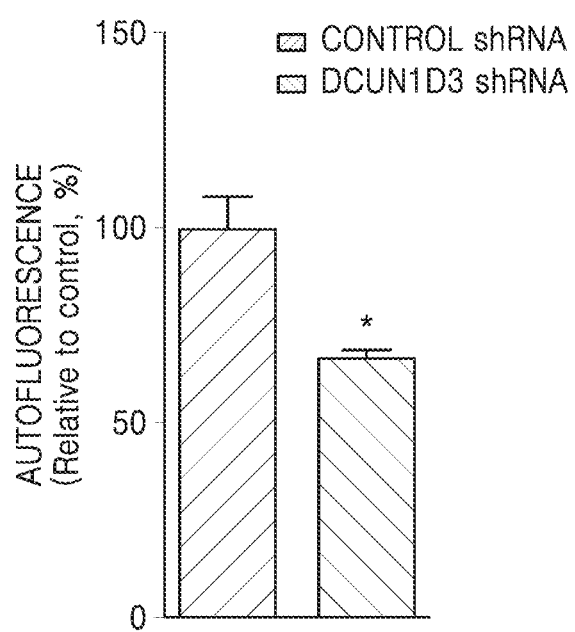
FIG. 3 shows the amount of lipofuscin according to fluorescence intensity in senescent cells transfected with DCUN1D3 shRNA or scrambled shRNA-containing lentivirus.

The amount of lipofuscin in the cultured senescent cells was measured by autofluorescence. FIG. 3 shows results of measuring the amount of lipofuscin in the senescent cells transfected with DCUN1D3 shRNA or scrambled shRNA-containing lentivirus.

As shown in FIG. 3, an autofluorescence level of the senescent cells transfected with DCUN1D3 shRNA-containing lentivirus was about 66%, compared to that of the senescent cells transfected with scrambled shRNA-containing lentivirus. Therefore, it is confirmed that lipofuscin accumulation was reduced in senescent cells by transfection of the cells with DCUN1D3 shRNA-containing lentivirus, indicating that a cellular senescence level is reduced by transfection of senescent cells with DCUN1D3 shRNA-containing lentivirus.

Figure 4:
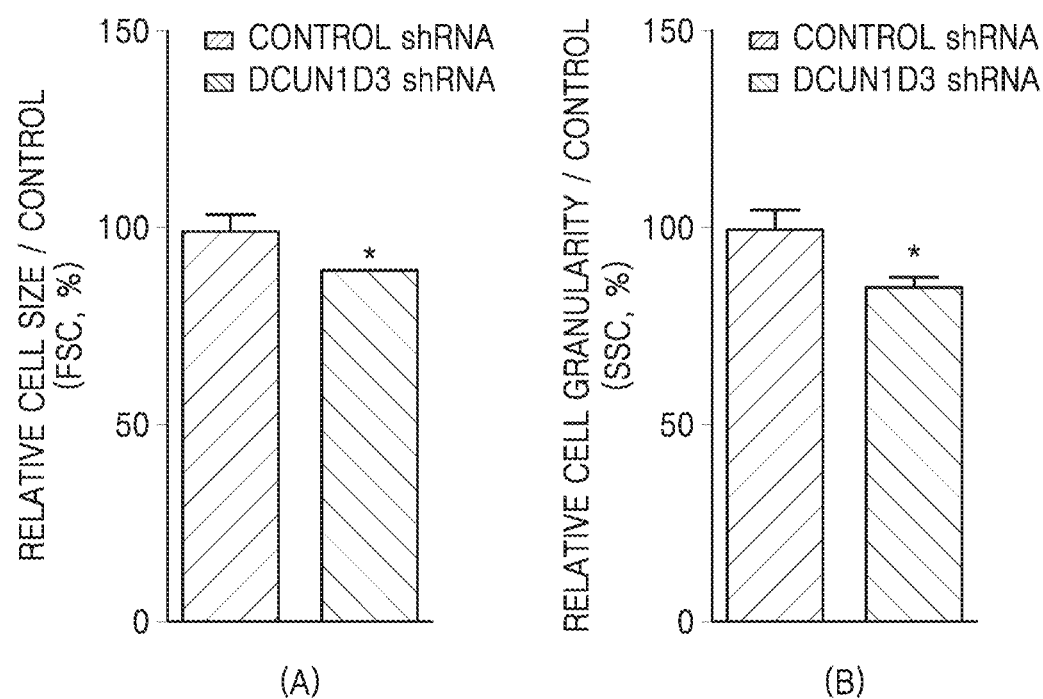
FIG. 4 shows relative cell size of senescent cells (% of control) transfected with DCUN1D3 shRNA-containing lentivirus or scrambled shRNA-containing lentivirus.

FIG. 4 shows results of measuring the size of the senescent cells transfected with DCUN1D3 shRNA or scrambled shRNA-containing lentivirus. As shown in FIG. 4, the size of the senescent cells transfected with DCUN1D3 shRNA-containing lentivirus was smaller than that of the senescent cells transfected with scrambled shRNA-containing lentivirus.

In FIG. 4, the size, granularity, and autofluorescence of the cells were estimated by flow cytometry. In detail, trypsin-treated cells were collected in PBS, and analyzed by FACS Caliber instrument (Becton Dickson, USA). The size and granularity of 100,000 cells were evaluated by previous forward and side scatter. Autofluorescence was measured using a 488-nm laser for excitation and a 530/30 bandpass filter for detection. FSC and SSC in the vertical axis of A and B of FIG. 4 represent forward scatter (cell size) and side scatter (cell granularity), respectively.

(4) Influence on Cell Cycle Regulation

With senescence, the proportion of cells in the G0/G1 phase increases, and cells in the S phase and G2/M phase decreases.

To confirm this, senescent cells were introduced with siRNA and control siRNA, and cell cycle was examined. In detail, as explained in (1), siRNA and control siRNA were introduced into senescent cells by introducing it into senescent cells using lipofectamine without packaging shRNA or scrambled RNA in lentivirus, and the senescent cells were cultured and then cell cycle was examined. DCUN1D3 shRNA was introduced, and therefore, DCUN1D3 siRNA was allowed to produce within the cells.

Figure 5:
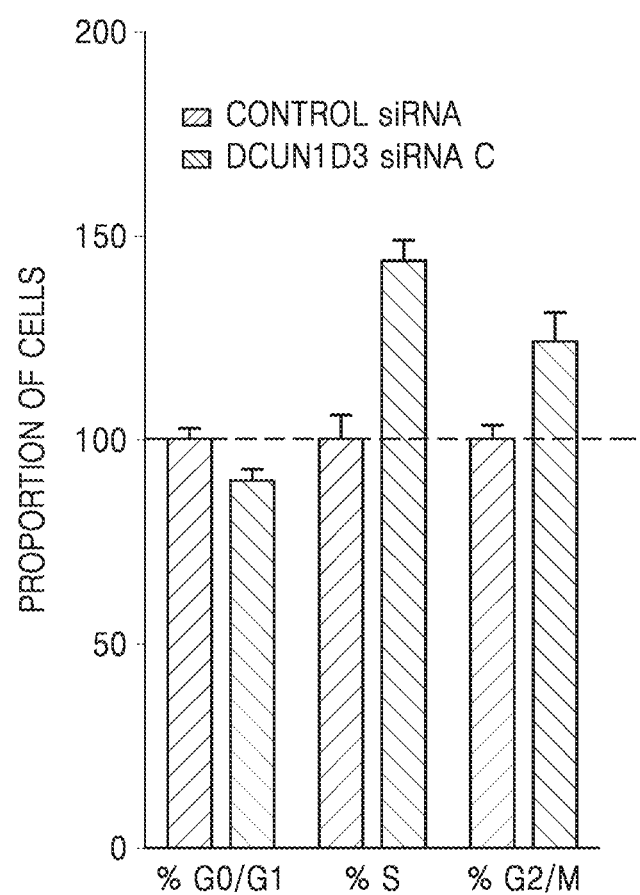
FIG. 5 shows the proportion of senescent cells introduced with DCUN1D3 siRNA or control siRNA in G0/G1, S, or G2/M phase of the cell cycle.

FIG. 5 shows results of measuring the cell cycle of the senescent cells introduced with DCUN1D3 siRNA or control siRNA. In FIG. 5, the experiment was performed in triplicate, and culture was performed for 3 days. As shown in FIG. 5, the senescent cells introduced with DCUN1D3 siRNA showed increased cell percentages in the G0/G1 phase and increased cell percentages in the S phase and G2/M phase, compared to the senescent cells introduced with control siRNA. The unit of the vertical axis of FIG. 5 is %, which is a percentage when the result of control siRNA is taken as 100.

TABLE 1

| | Cell cycle | | |
| --- | --- | --- | --- |
| | % G0/G1 | % S | % G2/M |
| Control siRNA | 66.83 | 5.50 | 23.87 |
| DCUN1D3 siRNA | 60.10 | 7.90 | 29.65 | n = 3, 3 day-culture, HDF (M4, doubling time = 14 days).

Example 2: Effects of DCUN1D3 shRNA or siRNA and/or shSEAT1 or siSEAT1 on Senescent Cells In this Example, correlation of intracellular levels of DCUN1D3 and SEAT1 was examined, and their effects on senescent cells were examined.

(1) Induction of Senescent Cell Proliferation

DCUN1D3 shRNA or SEAT1 (senescence-associated transcript1) shRNA was transduced into senescent cells to examine their effects on proliferation of senescent cells. Senescent cells to be used were prepared by subculturing human dermal fibroblast (HDF) M4 cells obtained from a 4-year-old boy (derived from the foreskin of a 4-year-old donor, Seoul National University) in DMEM (hereinafter, referred to as DMEM') (HyClone, Logan, Utah, USA: Cat no. SH30243) containing high concentration of glucose, glutamine, and pyruvate and being supplemented with 10%

(v/v) fetal bovine serum (FBS), and 1× penicillin/streptomycin (100 U/ml penicillin, 100 ug/ml streptomycin) under conditions of 37° C. and 5% $CO_2$. The used senescent cells were at passage 33 and the cell doubling time was about 14 days or longer.

DCUN1D3 shRNA or SEAT1 shRNA was introduced into lentivirus to prepare a DCUN1D3 shRNA or SEAT1 shRNA-containing lentivirus, which was transduced into the senescent cells. The DCUN1D3 shRNA or SEAT1 shRNA-containing lentiviral pLKO.1 puro vector (OriGene, USA) was prepared by synthesizing nucleotide sequences of SEQ ID NOS: 1 and 2, respectively to prepare a double stranded shRNA construct (IDT, Korea), and ligating the shRNA construct into pLKO.1 puro vector digested with restriction enzymes AgeI and EcoRI. The prepared DCUN1D3 shRNA or SEAT1 shRNA-containing lentivirus was transduced into 293FT human embryonic kidney cells (#R700-07: Invitrogen) using Lipofectamine 2000, together with packaging vectors, VSV-G and PAX2 (OriGene, USA). Herein, during the transduction, 6 ug/ml polybrene was added to the growth medium for kidney cells to increase the transduction efficiency. On day 2 after transduction, a lentiviral supernatant was collected and concentrated using Lenti-X (Clontech, cat. no.631231).

The DCUN1D3 shRNA or SEAT1 shRNA-containing lentivirus thus prepared was transfected into the senescent cells and subcultured in DMEM (hereinafter, referred to as DMEM) (HyClone, cat. no. SH30243, USA) containing high concentration of glucose, glutamine, and pyruvate and being supplemented with 10% (v/v) fetal bovine serum (FBS), and 1× penicillin/streptomycin (100 U/ml penicillin, 100 ug/ml streptomycin) for 4 weeks under conditions of 37° C. and 5% $CO_2$. The nucleotide sequence of the used DCUN1D3 shRNA was a nucleotide sequence of SEQ ID NO: 1 (sense) and SEQ ID NO: 2 (antisense). The nucleotide sequence of the used SEAT1 shRNA was a nucleotide sequence of SEQ ID NO: 6 and a polynucleotide of SEQ ID NO: 7 (SEAT1 siRNA #1); a nucleotide sequence of SEQ ID NO: 8 and a polynucleotide of SEQ ID NO: 9 (SEAT1 siRNA #2); or a nucleotide sequence of SEQ ID NO: 10 and a polynucleotide of SEQ ID NO: 11 (SEAT1 siRNA #3). Scrambled RNA (Bioneer, Korea) used as a control group was provided by the manufacturer.

```
DCUN1D3 shRNA:
SEQ ID NO: 1 (sense):
GUCACUGCAUCGGGAAAUA(dTdT)

SEQ ID NO: 2 (antisense):
UAUUUCCCGAUGCAGUGAC(dTdT)
```

SEAT1 #1 shRNA:

SEAT1 siRNA #1; polynucleotide of SEQ ID NO: 6 (sense) and SEQ ID NO: 7 (antisense)

SEAT1 siRNA #2; polynucleotide of SEQ ID NO: 8 (sense) and SEQ ID NO: 9 (antisense)

SEAT1 siRNA #3; polynucleotide of SEQ ID NO: 10 (sense) and SEQ ID NO: 11 (antisense)

Figure 6:
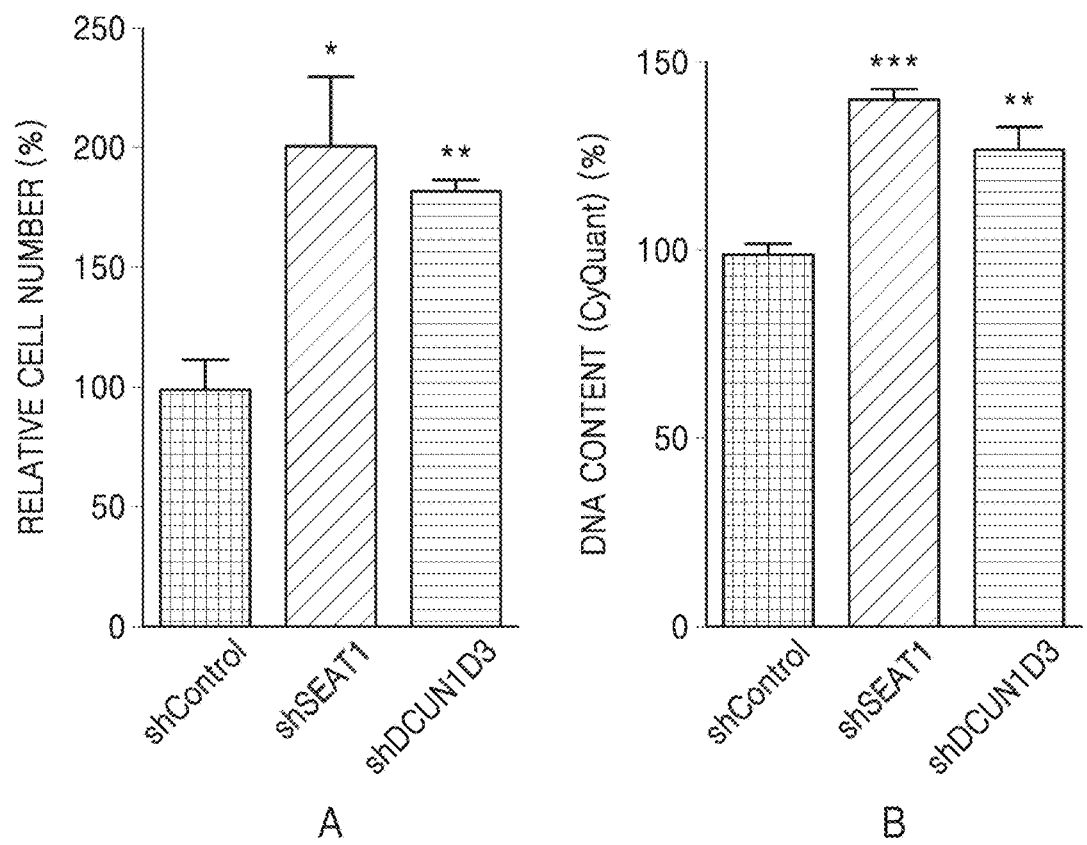
FIG. 6 shows the relative number (A) and DNA content of cultured senescent cells transfected with DCUN1D3 shRNA or SEAT1 shRNA-containing lentivirus.

FIG. 6 shows the relative number (A) and DNA content of cultured senescent cells transfected with DCUN1D3 shRNA or SEAT1 shRNA-containing lentivirus. In FIG. 6, "control shRNA" represents senescent cells transfected with scramble shRNA-containing lentivirus, and "DCUN1D3 shRNA" and "SEAT1 shRNA" represent senescent cells transfected with DCUN1D3 shRNA (SEQ ID NOs: 1 and 2) or SEAT1 shRNA (SEQ ID NOs: 6 and 7)-containing lentivirus, respectively. As shown in FIG. 6, the senescent cells transfected with DCUN1D3 shRNA or SEAT1 shRNA-containing lentivirus showed increases in the number of cells and DNA content, compared to senescent cells transfected with scramble shRNA-containing lentivirus, namely, a negative control group. Further, their cell morphology was the same as that of young cells. Therefore, it can be seen that introduction of DCUN1D3 shRNA or SEAT1 shRNA into senescent cells induces proliferation of senescent cells. In FIG. 6, the DNA content was measured as follows. The cells were seeded in a flat-bottomed 6-well microplate at a density of 20,000 cells/well. The number of cells was determined by measuring SYBR Gold (Invitrogen) fluorescence intensity in a fluorstar microplate reader (BMG Labtec, Cary, N.C., USA) at a predetermined time.

(2) Reduction of Activity of Senescence-Associated Beta-Galactosidase (SA β-Gal)

Senescent cells were stained blue with X-gal due to increased activity of SA β-gal. As explained in (1), senescent cells were transfected with DCUN1D3 shRNA or SEAT1 shRNA or scramble shRNA-containing lentivirus, and SA β-gal activity in the cultured senescent cells was measured. Senescent cells that were transfected with none of DCUN1D3 shRNA or SEAT1 shRNA or scramble shRNA-containing lentivirus were used as a negative control group.

Figure 7:
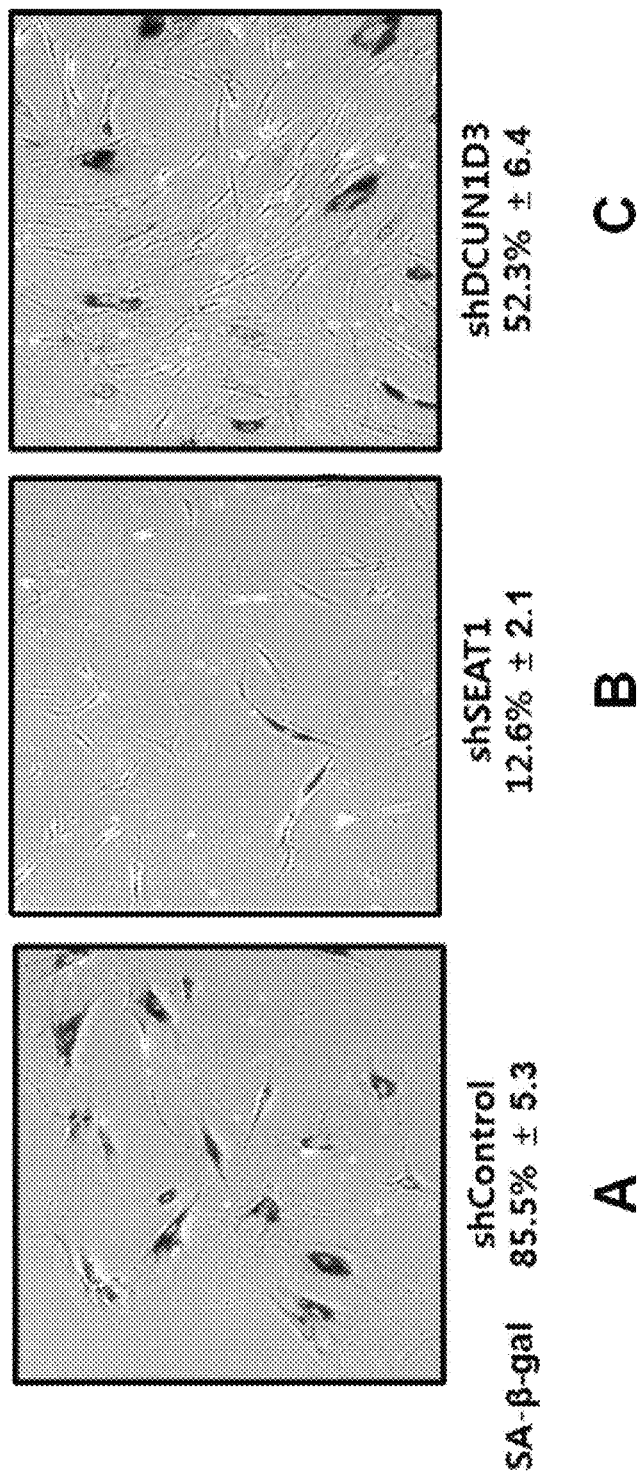
FIG. 7 shows an X-gal staining image of senescent cells transfected with scramble shRNA(A) or SEAT1 shRNA(B) or DCUN1D3 shRNA(C)-containing lentivirus, and a percentage (%) of the cells stained blue.

In detail, the cultured senescent cells were stained using a cellular senescence assay kit (Cell BIOLABS, INC.) according to the manufacturer's instructions, and the number of cells stained blue was counted under a microscope. FIG. 7 shows an X-gal staining image of senescent cells transfected with scramble shRNA(A) or SEAT1 shRNA(B) or DCUN1D3 shRNA(C)-containing lentivirus, and a percentage (%) of the cells stained blue.

As shown in FIG. 7, about 85.5% of the senescent cells transfected with scrambled shRNA-containing lentivirus were stained, whereas about 52% and about 12.6% of the senescent cells transfected with DCUN1D3 shRNA and SEAT1 shRNA-containing lentivirus were stained, respectively. Therefore, it is confirmed that SA β-gal activity was reduced by transfection of senescent cells with DCUN1D3 shRNA and/or SEAT1 shRNA-containing lentivirus, indicating that a cellular senescence level is reduced by transfection of senescent cells with DCUN1D3 shRNA and/or SEAT1 shRNA-containing lentivirus.

(3) Reduction in Autophagy Activity and Reduction in Lipofuscin Accumulation

It is known that senescent cells show a reduction in autophagy activity, accumulation of lipofuscin, and mitochondrial damage. In order to examine this, as described in (1), senescent cells were transfected with DCUN1D3 shRNA or SEAT1 shRNA or scramble shRNA-containing lentivirus, and the amount of lipofuscin was measured in the cultured senescent cells. Senescent cells that were transfected with none of DCUN1D3 shRNA or SEAT1 shRNA or scramble shRNA-containing lentivirus were used as a negative control group. Further, the size of the cell was measured.

Figure 8:
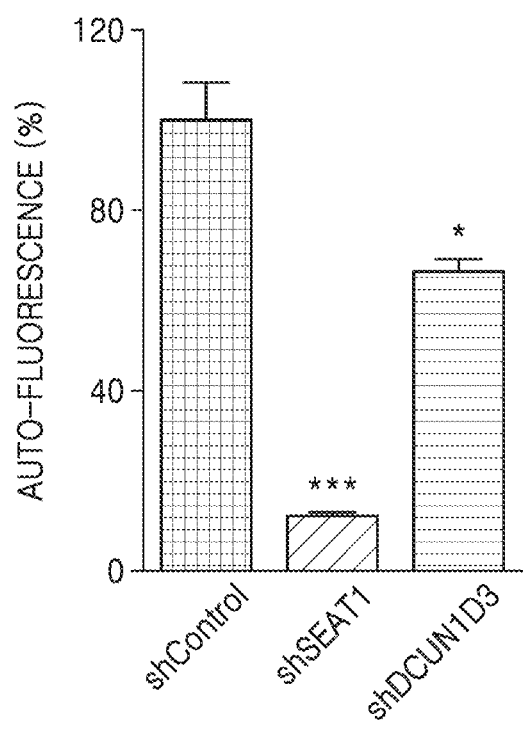
FIG. 8 shows results of measuring lipofuscin in senescent cells transfected with DCUN1D3 shRNA or SEAT1 shRNA or scramble shRNA-containing lentivirus.

The amount of lipofuscin in the cultured senescent cells was measured by autofluorescence. FIG. 8 shows results of measuring the amount of lipofuscin in the senescent cells transfected with DCUN1D3 shRNA or SEAT1 shRNA or scramble shRNA-containing lentivirus.

As shown in FIG. 8, an autofluorescence level of the senescent cells transfected with SEAT1 shRNA or DCUN1D3 shRNA-containing lentivirus was about 10% and about 66%, respectively, compared to that of the senescent cells transfected with scrambled shRNA-containing lentivirus. Therefore, it is confirmed that lipofuscin accumulation was reduced in senescent cells by transfection of the cells with SEAT1 shRNA or DCUN1D3 shRNA-containing lentivirus, indicating that a cellular senescence level is reduced by transfection of senescent cells with SEAT1 shRNA or DCUN1D3 shRNA-containing lentivirus.

Figure 9:
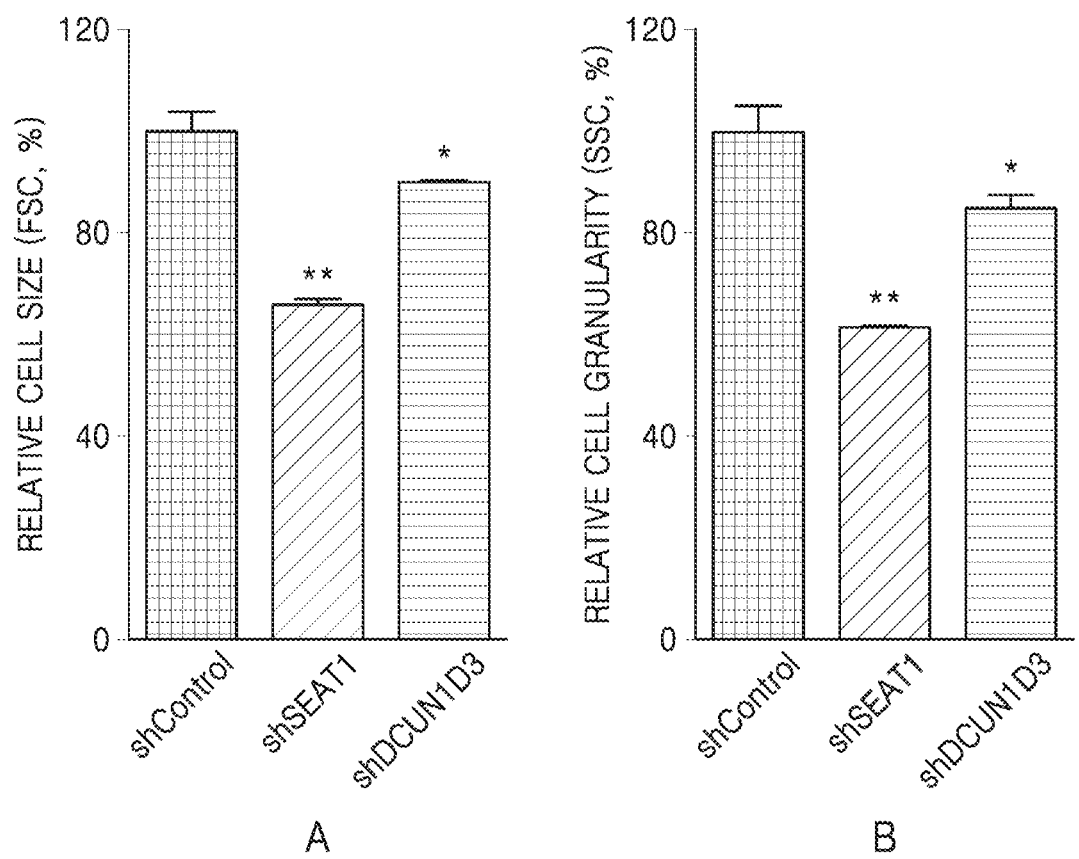
FIG. 9 shows results of measuring cell size (A) and cell granularity (B) of senescent cells transfected with DCUN1D3 shRNA or SEAT1 shRNA or scramble shRNA-containing lentivirus.

FIG. 9 shows results of measuring cell size (A) and cell granularity (B) of senescent cells transfected with DCUN1D3 shRNA or SEAT1 shRNA or scramble shRNA-containing lentivirus. As shown in FIG. 9, the size of the senescent cells transfected with DCUN1D3 shRNA or SEAT1 shRNA-containing lentivirus was smaller than that of the senescent cells transfected with scrambled shRNA-containing lentivirus.

In FIGS. 8 and 9, the size, granularity, and autofluorescence of the cells were estimated by flow cytometry. In detail, trypsin-treated cells were collected in PBS, and analyzed by FACS Caliber instrument (Becton Dickson, USA). The size and granularity of 100,000 cells were evaluated by previous forward and side scatter. Autofluorescence was measured using a 488-nm laser for excitation and a 530/30 bandpass filter for detection. FSC and SSC in the vertical axis of A and B of FIG. 9 represent forward scatter (cell size) and side scatter (cell granularity), respectively.

(4) Influence on Cell Cycle Regulation

With senescence, cells in the G0/G1 phase increases, and cells in the S phase and G2/M phase decreases.

To confirm this, senescent cells were introduced with siRNA and control siRNA, and cell cycle was examined. In detail, as explained in (1), siRNA and control siRNA were introduced into senescent cells by introducing it into senescent cells using lipofectamine without packaging shRNA or scrambled RNA in lentivirus, and the senescent cells were cultured and then cell cycle was examined. SEAT1 siRNA and DCUN1D3 siRNA were introduced, respectively and therefore, SEAT1 siRNA and DCUN1D3 siRNA were allowed to produce within the cells.

Figure 10:
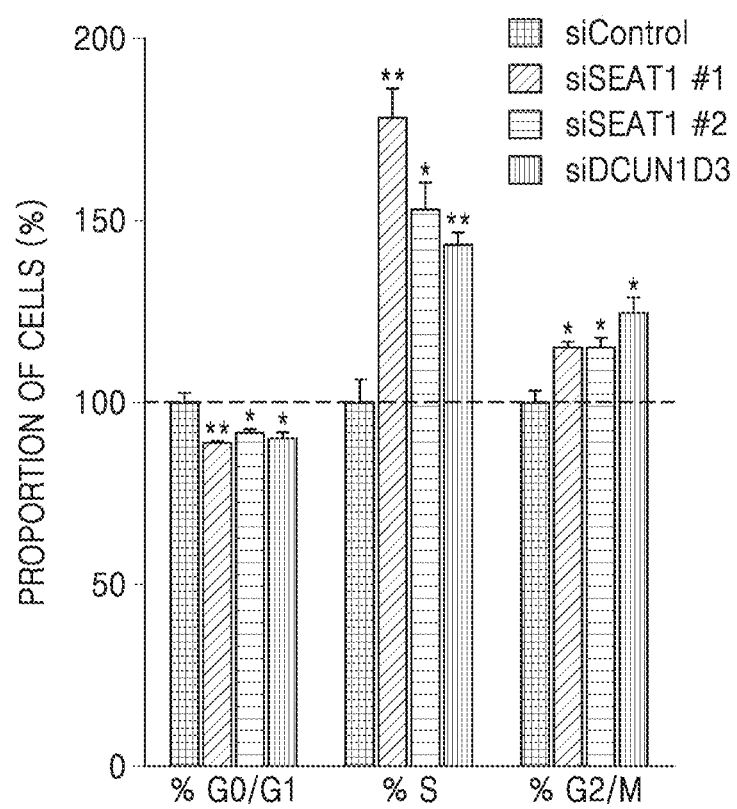
FIG. 10 shows results of measuring cell cycle of senescent cells transfected with SEAT1 siRNA or DCUN1D3 siRNA or control siRNA.

FIG. 10 shows results of measuring the cell cycle of the senescent cells introduced with SEAT1 siRNA or DCUN1D3 siRNA or control siRNA. In FIG. 10, the experiment was performed in triplicate, and culture was performed for 3 days. As shown in FIG. 10, the senescent cells introduced with SEAT1 siRNA or DCUN1D3 siRNA showed decreased cell percentages in the G0/G1 phase and increased cell percentages in the S phase and G2/M phase, compared to the senescent cells introduced with control siRNA. The unit of the vertical axis of FIG. 10 is %, which is a percentage when the result of control siRNA is taken as 100.

TABLE 2

| | Cell cycle | | |
|---|---|---|---|
| | % G0/G1 | % S | % G2/M |
| Control siRNA | 66.8 | 5.5 | 23.9 |
| DCUN1D3 siRNA | 60.1 | 7.9 | 29.7 |
| SEAT1 shRNA #1 | 59.4 | 9.8 | 27.5 |
| SEAT1 shRNA #2 | 61.4 | 8.4 | 27.5 | n = 3, 3 day-culture, HDF (M4, doubling time = 14 days).

The sequence of SEAT1 shRNA #2 is as follows.
SEAT1 #2 shRNA:
SEAT1 siRNA #2; polynucleotide of SEQ ID NO: 8 (sense) and SEQ ID NO: 9 (antisense)

(5) DCUN1D3 as Target Protein of SEAT1

It was examined whether DCUN1D3 gene is a target of an Lnc RNA, SEAT1.

First, it was examined whether expression of DCUN1D3 gene is reduced by introduction of human cells and mouse cells with siSEAT1. The used human cells were senescent HDF M4 cells used in (1), and the mouse cells were MEF (mouse embryo fibroblast) cells. The introduction of siRNA into cells was performed in the same manner as in (4).

Figure 11:
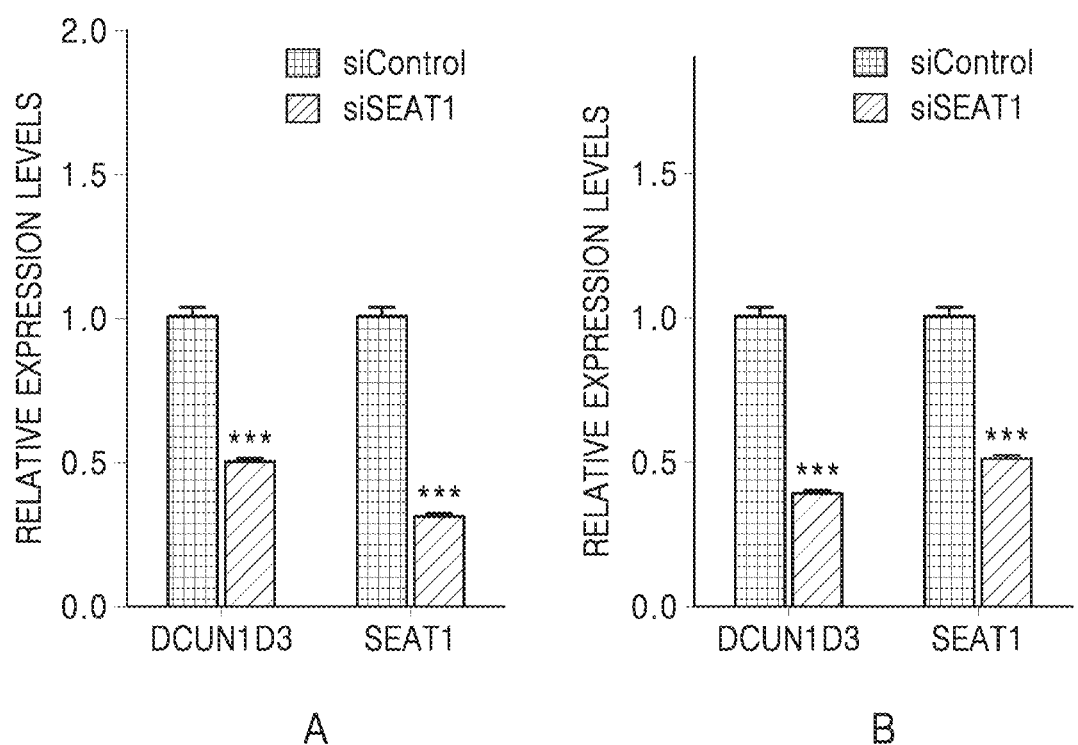
FIG. 11 shows expression levels of DCUN1D3 gene and SEAT1 gene in human cells (A) and mouse cells (B) introduced with siSEAT1.

FIG. 11 shows expression levels of DCUN1D3 gene and SEAT1 gene in human cells (A) and mouse cells (B) introduced with siSEAT1. As shown in FIG. 11, when SEAT1 siRNA was introduced, expression of DCUN1D3 gene as well as expression of SEAT1 gene was reduced, indicating that expression of DCUN1D3 gene is strongly associated with expression of SEAT1 gene. That is, DCUN1D3 gene is a target of SEAT1.

(6) Effect of SEAT1 and DCUN1D3 on DNA Damage DNA

It was examined whether SEAT1 and DCUN1D3 decrease or increase DNA damages.

In detail, each of SEAT1 shRNA and DCUN1D3 shRNA was introduced into senescent HDF M4 cells described in (1) according to the method described in (1), and cultured. Then, monoclonal antibodies specific to DNA damage markers, vH2AX and 53BP1 were used to examine vH2AX and/or 53BP1-positive cells. In detail, cells were grown on a poly-L-lysine-coated cover slip (#08-774-383; Corning Inc., Corning N.Y., USA) or in a 35-mm dish (#81156: Corning Inc.). Cells were fixed with 2% paraformaldehyde in fresh PBS at room temperature for 10 to 20 minutes, and then permeabilized with 0.5% Triton X-100 and 2 ug/ml Hoechst 33342(Sigma-Aldrich) in PBS for 5 minutes. Blocking was performed at room temperature for 30 minutes using 2% BSA in PBS. The sample was incubated with primary antibodies diluted with 2% BSA/PBS-d at room temperature for 1 to 2 hr or overnight, and washed with PBS. Then, the sample was incubated with secondary antibodies (Jackson ImmunoResearch) for 30 minutes. Next, the sample was mounted using a ProLong Gold Antifade reagent (Invitrogen), followed by storing at −30° C. or immediate imaging. Fluorescence signals were visualized using a Zeiss AxioObserver D1 or Zeiss 710 confocal microscope (Wetzlar, Germany). The results are given in FIG. 12.

Figure 12:
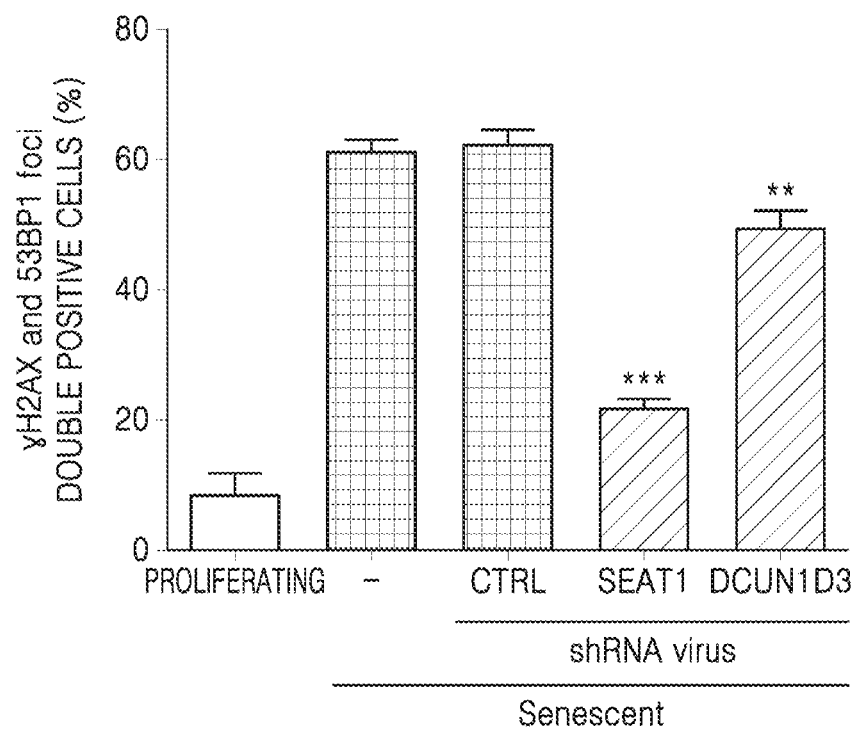
FIG. 12 shows effects of SEAT1 shRNA and/or DCUN1D3 shRNA on intracellular DNA damage.

FIG. 12 shows effects of SEAT1 shRNA and/or DCUN1D3 shRNA on intracellular DNA damage. As shown in FIG. 12, when SEAT1 shRNA or DCUN1D3 shRNA is introduced into senescent cells, DNA damage was remarkably reduced, indicating that SEAT1 shRNA or DCUN1D3 shRNA converts senescent cells into young cells, or protects senescent cells, and also indicating that SEAT1 shRNA or DCUN1D3 shRNA may prevent or treat a senescence-associated disease or symptom. In FIG. 12, "Proliferating" represents HDF M4 cells. The vertical axis in FIG. 12 represents a percentage of vH2AX and 53BP1-double positive cells. As this value is higher, DNA damage is higher.

(7) Effect of Inhibition of SEAT1 or DCUN1D3 Gene Expression on hIL-6 Expression Effect of inhibition of SEAT1 or DCUN1D3 gene expression on hIL-6 expression was examined. IL-6 (interleukin-6) is a pro-inflammatory cytokine, and expressed by IL6 gene in human. It is known that senescent cells show a higher IL-6 level than young cells. A reduction in the intracellular IL-6 level may be an index of an ability to protect senescent cells or to convert senescent cells into young cells.

In detail, each of SEAT1 siRNA and DCUN1D3 siRNA was introduced into senescent HDF M4 cells described in (1) according to the method described in (1), and cultured. Then, monoclonal antibodies specific to hIL-6 were used to perform ELISA, and hIL-6 levels in the culture supernatant were measured by Luminex. The results are given in FIG. 13.

Figure 13:
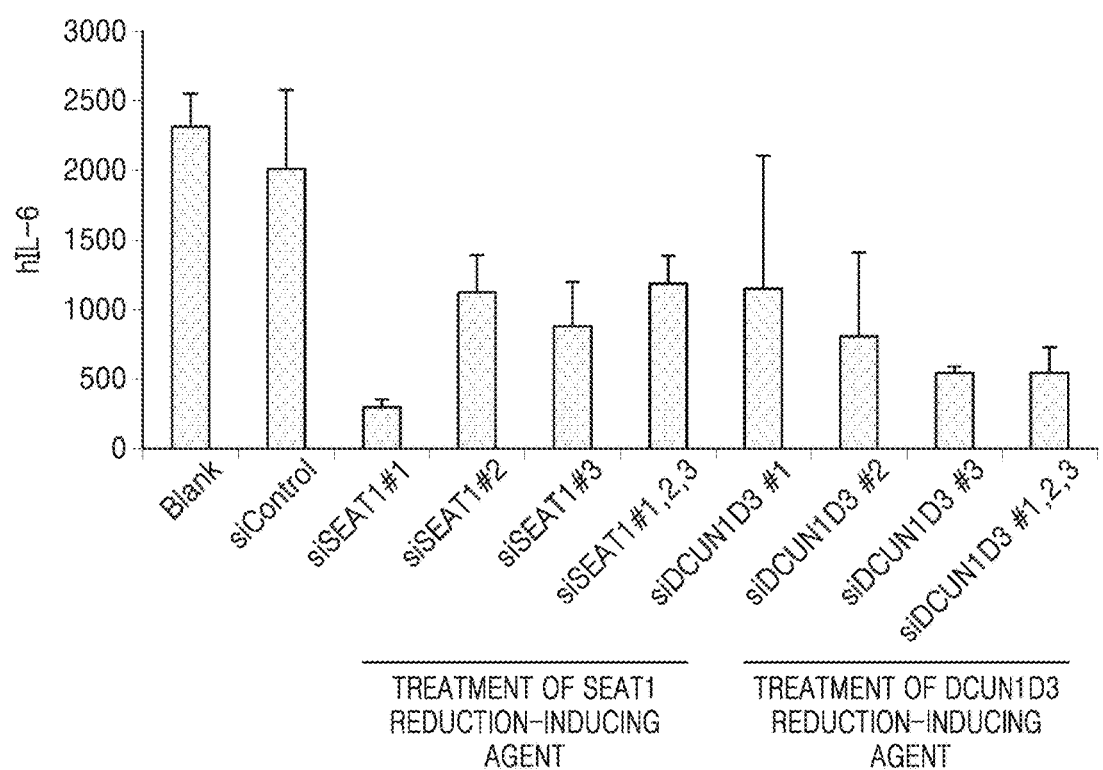
FIG. 13 shows effects of SEAT1 or DCUN1D3 gene expression inhibition on hIL-6 expression.

FIG. 13 shows effects of SEAT1 or DCUN1D3 gene expression inhibition on hIL-6 expression. In FIG. 13, siSEAT1 #3, DCUN1D3 #2, and #3 represent siRNAs formed from shRNAs having the following sequences. Further, siSEAT1 #1,2,3 and siDCUN1D3 #1,2,3 represent co-introduction of three siRNAs, respectively.

SEAT1 #3 shRNA:
Polynucleotide of SEQ ID NO: 10 (sense)
Polynucleotide of SEQ ID NO: 11 (antisense)
DCUN1D3 #2 shRNA:
Polynucleotide of SEQ ID NO: 12 (sense)
Polynucleotide of SEQ ID NO: 13 (antisense)
DCUN1D3 #3 shRNA:
Polynucleotide of SEQ ID NO: 14 (sense)
Polynucleotide of SEQ ID NO: 15 (antisense)

As shown in FIG. 13, when siRNAs of SEAT1 and/or DCUN1D3 were introduced into senescent cells, the hIL-6 levels were remarkably reduced, indicating that shRNAs of SEAT1 and/or DCUN1D3 may convert senescent cells into young cells, protect senescent cells, or prevent or treat a senescence-associated disease or symptom of a subject.

(8) Regulation of DCUN1D3 Gene Expression by miR-20b miR-20b (SEQ ID NO: 16) involved in the regulation of DCUN1D3 gene expression was identified by comparing the sequences of SEAT1 and DCUN1D3 genes with the known miRNA sequences.

In detail, miR-20b was introduced into senescent HDF M4 cells described in (1) according to the method described in (1), and cultured. Then, monoclonal antibodies specific to DCUN1D3 were used to perform ELISA, and DCUN1D3 levels in the cells were measured. Specifically, miR-20b was transfected into senescent HDF M4 cells according to the following method, and cultured for 3 days. The cells were harvested and RNA was extracted therefrom. The extracted RNA was used as a template to perform RT-PCR, and DCUN1D3 mRNA levels were measured: The transfection of HDF M4 cells was performed using 50 nM siRNA mixed with Lipofectamine RNAiMAX (Invitrogen, Carlsbad, Calif., USA) in accordance with the manufacturer's instructions. 3 days after transfection, cells were harvested and RNA was extracted therefrom. A miR-20b gain-of-function study was performed using miR-20b mimics (50 nM) and its negative control (50 nM) on the HDF M4 cells. The loss-of-function study was performed with miR-20b inhibitor (75 nM) and its negative control (75 nM) on the HDF M4 cells. The results are given in FIG. 14.

Figure 14:
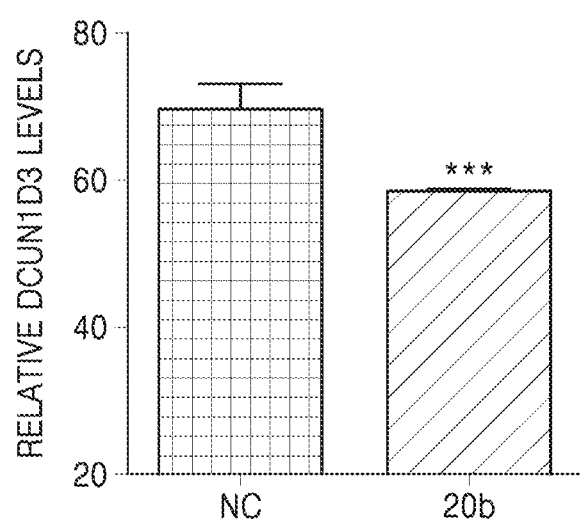
FIG. 14 shows effects of miR-20b on DCUN1D3 gene expression.

FIG. 14 shows effects of miR-20b on DCUN1D3 gene expression. In FIG. 14, the vertical axis represents relative DCUN1D3 levels. As shown in FIG. 14, when miR-20b was introduced into senescent cells, DCUN1D3 expression was remarkably reduced.

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. A method of reducing cellular senescence in a mammal in need thereof, the method comprising administering to the mammal a non-natural composition comprising an activity inhibitor inhibiting activity of one or more of DCN1, defective in cullin neddylation 1, domain containing 3 (DCUN1D3) protein and a polynucleotide having a nucleotide sequence of SEQ ID NO: 5, or an expression inhibitor that inhibits expression of one or more of a gene encoding DCUN1D3 and a gene encoding the nucleotide sequence of SEQ ID NO: 5,
wherein the composition reduces markers of cellular senescence when administered to a cell; the expression inhibitor is a vector encoding a small hairpin RNA (shRNA) comprising a nucleotide sequence of SEQ ID NO: 1 and a nucleotide sequence of SEQ ID NO: 2; and the activity inhibitor is small interference RNA (siRNA) against a polynucleotide having a nucleotide sequence of SEQ ID NO: 5, comprising polynucleotides of SEQ ID NO: 10 and 11, SEQ ID NO:12 and 13, or SEQ ID NO: 14 and 15.

2. A method of treating a disease or a disease symptom associated with increased cellular senescence in a mammal with said disease or disease symptom, the method comprising administering to the mammal a non-natural composition comprising an activity inhibitor inhibiting activity of one or more of DCN1, defective in cullin neddylation 1, domain containing 3 (DCUN1D3) protein and a polynucleotide having a nucleotide sequence of SEQ ID NO: 5, or an expression inhibitor inhibiting expression of one or more of a gene encoding DCUN1D3 and a gene encoding the nucleotide sequence of SEQ ID NO: 5,
wherein the composition reduces markers of cellular senescence when administered to a cell; the expression inhibitor is a vector encoding a small hairpin RNA (shRNA) comprising a nucleotide sequence of SEQ ID NO: 1 and a nucleotide sequence of SEQ ID NO: 2; and the activity inhibitor is small interference RNA (siRNA) against a polynucleotide having a nucleotide sequence of SEQ ID NO: 5, comprising polynucleotides of SEQ ID NO: 10 and 11, SEQ ID NO:12 and 13, or SEQ ID NO: 14 and 15.

3. The method of claim 2, wherein the disease or the disease symptom associated with increased cellular senescence level is skin wrinkles, wound healing declines, sarcopenia, muscular dystrophy, early senescent symptom (Hutchinson-Gilford progeria syndrome), or a combination thereof.

4. The method of claim 2, wherein the disease or the disease symptom associated with increased cellular senescence level is a disease or a disease symptom associated with accumulation of lipofuscin.

5. The method of claim 4, wherein the disease or the disease symptom associated with accumulation of lipofuscin is neuronal ceroid lipofuscinoses (NCL), age related macular degeneration, neurofibrillary tangles, brown atrophy of the heart, Alzheimer's disease, Parkinson's disease, amyotrophic lateral sclerosis (ALS), acromegaly, denervation atrophy, lipid myopathy, or chronic obstructive pulmonary disease (COPD).

6. A method of reducing a lipofuscin level in a mammalian cell, the method comprising administering to a mammal in need thereof a non-natural composition comprising an activity inhibitor inhibiting activity of one or more of DCN1, defective in cullin neddylation 1, domain containing 3 (DCUN1D3) protein and a polynucleotide having a nucleotide sequence of SEQ ID NO: 5, or an expression inhibitor inhibiting expression of one or more of a gene encoding DCUN1D3 and a gene encoding the nucleotide sequence of SEQ ID NO: 5, wherein the composition reduces markers of cellular senescence when administered to a cell; the expression inhibitor is a vector encoding a small hairpin RNA (shRNA) comprising a nucleotide sequence of SEQ ID NO: 1 and a nucleotide sequence of SEQ ID NO: 2; and the activity inhibitor is small interference RNA (siRNA) against a polynucleotide having a nucleotide sequence of SEQ ID NO: 5, comprising polynucleotides of SEQ ID NO: 10 and 11, SEQ ID NO:12 and 13, or SEQ ID NO: 14 and 15.

7. The method of claim 6, wherein the method is used to treat a disease or a disease symptom associated with increased lipofuscin level in a mammalian cell.

* * * * *

SEQUENCE LISTING

```
<160> NUMBER OF SEQ ID NOS: 16

<210> SEQ ID NO 1
<211> LENGTH: 21
<212> TYPE: DNA
<213> ORGANISM: Artificial Sequence
<220> FEATURE:
<223> OTHER INFORMATION: Synthetic shRNA: sense sequence
<220> FEATURE:
<221> NAME/KEY: misc_feature
<222> LOCATION: (1)..(19)
<223> OTHER INFORMATION: nucleotide sequence (RNA)
<220> FEATURE:
<221> NAME/KEY: misc_feature
<222> LOCATION: (20)..(21)
<223> OTHER INFORMATION: deoxynucleotide sequence (DNA)

<400> SEQUENCE: 1
gucacugcau cgggaaauat t                                              21

<210> SEQ ID NO 2
<211> LENGTH: 21
<212> TYPE: DNA
<213> ORGANISM: Artificial Sequence
<220> FEATURE:
<223> OTHER INFORMATION: Synthetic shRNA: antisense sequence
<220> FEATURE:
<221> NAME/KEY: misc_feature
<222> LOCATION: (1)..(19)
<223> OTHER INFORMATION: nucleotide sequence (RNA)
<220> FEATURE:
<221> NAME/KEY: misc_feature
<222> LOCATION: (20)..(21)
<223> OTHER INFORMATION: deoxynucleotide sequence (DNA)
```

<400> SEQUENCE: 2
uauuucccga ugcagugact t                                                    21

<210> SEQ ID NO 3
<211> LENGTH: 304
<212> TYPE: PRT
<213> ORGANISM: Homo sapiens
<220> FEATURE:
<221> NAME/KEY: misc_feature
<222> LOCATION: (1)..(304)
<223> OTHER INFORMATION: DCN1-like protein 3

<400> SEQUENCE: 3

```
Met Gly Gln Cys Val Thr Lys Cys Lys Asn Pro Ser Ser Thr Leu Gly
1               5                   10                  15

Ser Lys Asn Gly Asp Arg Glu Pro Ser Asn Lys Ser His Ser Arg Arg
            20                  25                  30

Gly Ala Gly His Arg Glu Glu Gln Val Pro Pro Cys Gly Lys Pro Gly
        35                  40                  45

Gly Asp Ile Leu Val Asn Gly Thr Lys Lys Ala Glu Ala Ala Thr Glu
    50                  55                  60

Ala Cys Gln Leu Pro Thr Ser Ser Gly Asp Ala Gly Arg Glu Ser Lys
65                  70                  75                  80

Ser Asn Ala Glu Glu Ser Ser Leu Gln Arg Leu Glu Glu Leu Phe Arg
                85                  90                  95

Arg Tyr Lys Asp Glu Arg Glu Asp Ala Ile Leu Glu Glu Gly Met Glu
            100                 105                 110

Arg Phe Cys Asn Asp Leu Cys Val Asp Pro Thr Glu Phe Arg Val Leu
        115                 120                 125

Leu Leu Ala Trp Lys Phe Gln Ala Ala Thr Met Cys Lys Phe Thr Arg
    130                 135                 140

Lys Glu Phe Phe Asp Gly Cys Lys Ala Ile Ser Ala Asp Ser Ile Asp
145                 150                 155                 160

Gly Ile Cys Ala Arg Phe Pro Ser Leu Leu Thr Glu Ala Lys Gln Glu
                165                 170                 175

Asp Lys Phe Lys Asp Leu Tyr Arg Phe Thr Phe Gln Phe Gly Leu Asp
            180                 185                 190

Ser Glu Glu Gly Gln Arg Ser Leu His Arg Gly Ile Ala Ile Ala Leu
        195                 200                 205

Trp Lys Leu Val Phe Thr Gln Asn Asn Pro Val Leu Asp Gln Trp
    210                 215                 220

Leu Asn Phe Leu Thr Glu Asn Pro Ser Gly Ile Lys Gly Ile Ser Arg
225                 230                 235                 240

Asp Thr Trp Asn Met Phe Leu Asn Phe Thr Gln Val Ile Gly Pro Asp
                245                 250                 255

Leu Ser Asn Tyr Ser Glu Asp Glu Ala Trp Pro Ser Leu Phe Asp Thr
            260                 265                 270

Phe Val Glu Trp Glu Met Glu Arg Arg Lys Arg Glu Gly Glu Gly Arg
        275                 280                 285

Gly Ala Leu Ser Ser Gly Pro Glu Gly Leu Cys Pro Glu Glu Gln Thr
    290                 295                 300
```

<210> SEQ ID NO 4
<211> LENGTH: 2886
<212> TYPE: DNA
<213> ORGANISM: Homo sapiens

```
<220> FEATURE:
<221> NAME/KEY: misc_feature
<222> LOCATION: (1)..(2886)
<223> OTHER INFORMATION: DCN1, defective in cullin neddylation 1, domain
      containing 3 (DCUN1D3), mRNA

<400> SEQUENCE: 4
agaaagggtt tgactggagg aacctctgga gcagctgttg gctggctcct ctggctgatg      60
gcatgttgag gtacatgggc cagcggcagc gagggcatcc aatccagagg ggtccactct     120
agaggccagg ccaccagcac catgggccag tgtgtcacca agtgtaagaa tccctcatcg     180
accctgggca gcaaaaatgg agaccgtgag cccagcaaca agtcacatag caggaggggt     240
gcaggccacc gtgaggagca ggtaccaccc tgtggcaagc caggtggaga tatcctcgtc     300
aacgggacca agaaggccga ggctgccact gaggcctgcc agctgccaac gtcctcggga     360
gatgctggga gggagtccaa gtccaatgcc gaggagtctt ccttgcaaag attggaagaa     420
ctgttcaggc gctacaagga tgagcgggaa gatgcaattt tggaggaagg catggagcgc     480 tttttgcaatg acctgtgtgt tgaccccaca gaatttcgag tgctgctctt ggcttggaag     540
ttccaggctg caaccatgtg caaattcacc aggaaggagt tttttgatgg ctgcaaagca     600
ataagtgcag acagcattga cggaatctgt gcacggttcc ctagcctctt aacagaagcc     660
aaacaagagg ataaattcaa ggatctctac cggtttacat ttcagtttgg cctggactct     720
gaagaagggc agcggtcact gcatcgggaa atagccattg ccctgtggaa actagtcttt     780
acccagaaca atcctccggt attggaccaa tggctaaact tcctaacaga gaacccctcg     840
gggatcaagg gcatctcccg ggacacttgg aacatgttcc ttaacttcac tcaggtgatt     900
ggccctgacc tcagcaacta cagtgaagat gaggcctggc caagtctctt tgacaccttt     960
gtggagtggg aaatggagcg aaggaaaaga gaagggaag ggagaggtgc actcagctca    1020
gggcctgagg gcttgtgtcc cgaggagcag acttagtggc tctgtcccag gagcagcagc    1080
aaggatctgc cagctgccct gcagccaact gaggaattgg accattttgg aaattactga    1140
agatccggat attttctact ttacaccttt ctctgccttg tatctgaaag ggctctaaaa    1200
tgctgtatca tgttttaggc acttttcttca ttttttggt tattttggtt atttcctttt    1260
tggggggatc tcccagaata tttgaacctg gttacatgtt gtgtatcttt ttttgaagcc    1320
ttcagataga ataagcctgc catttcttgc acaaatttag gttttttttt tgtttttttt    1380
tgtttttttt tttttttttt tggtagggga gggcatagag cagggcgggg ggatgggact    1440
gttaggttga attaacatta caaaatgata cagtgccaga tctcagtttc gcatattgtt    1500
tttcagggca ggtctgtact gtgtgtagtg ctgtttacat agatgaattt aggttgtaat    1560 aattatttt aaagatttac acagatttga atagcagtgt taactgttaa ccacattgca    1620
ttaattccca ggcgatttag agctcttgga gagccaaggc cagccaagag catttgtagt    1680
ctggtgacaa ccccctttta agctaattta tccagaaccc tgatttccct cacttcttgc    1740
tcattccttc tttgacctat tgcatttcat gttgagtttt tccatcaaca tgctgcacct    1800
gtcagtcaag tgagcatttt ttaagaacac attgtactga gaaccactta agcattgaat    1860
gcggagaaag cagtgctacc tcagttttgc tggaagtaga cttctttgat agttttcttt    1920
ctttgatgaa gtttctgtat tttcatgttg taagtggaaa tacttttttt tgtttgtttg    1980
tttcatttgc cttggagcca aagtttctgt tcctggtggt cgggaaactg cctgccggcc    2040
aactgacttg aaggaaaact gtggtatgga gctctgcttg aattttttt ttttaatat    2100 ttttatttt ttctttgaat atcatcagct tacttgtctg gcaagggcag aagcctgggg    2160
```

```
ttggcctgaa ctctgccaaa caaatatcaa agtgtattta atagttaaat ttgtgccctt      2220
tcccttcttg ctgcacccat gttgtcactt aaccccagg agttatttat tatcttttg       2280 ttaaagtcag gctcatttgg ggtaatgtga tgactgttta ggtttacatg accctcctct      2340
cctttcccta cccccaaata tgtatatata catatataaa atatgtatat attttaccta      2400
tataaaatat atatatatac acatatatgt atctatattc ctttgtttct ttgcctgctt      2460
atactggcca taaagagggg agctgccttc aatgtataaa gtataagaag agtgccaggg      2520
aatgccataa tggaggcttt tggatctgaa tttggaccat ttcactaaag agaacatgag      2580
tttgctcagc cctttcctca caagaggag ggccccggtt ccccagactt ctccacgcgc       2640
tggctccata aaggccagct ttggccaggc tgccacaggg gcctgaggag ctcactctgg      2700
gcctacctgg tttcagttag agggtcctcc tgttattttt ccatttaaaa agtatgtcct      2760
cagaaaactg tactggaagg atgggtggca ggaacttgta tagttcagct tccaacactt      2820
tggaacagat taaaagggga atcttttaaa taaaaacgta taaaaataaa aaaaaaaaa       2880 aaaaaa                                                                 2886
```

<210> SEQ ID NO 5
<211> LENGTH: 2118
<212> TYPE: DNA
<213> ORGANISM: Homo sapiens

<400> SEQUENCE: 5

```
cttaatgagt gagcagtaag tctgtgtaag aggctgaatg catgcccctc agataagcca       60
gtacactcct tgcttagcaa cagaacatca gggtgatgtg gagaggggca ggatgtggac      120
gccacattgg aaatcggcaa catctgaggg caacaacaaa caagtgtgtt gggaaataag      180
aaataactca gttttgacaa ctggctttgt cagcttttgt gatgtttctt tagcagttta      240
ttggaaagat ggtatgagat gacgtgctgc ttcattgaat tgctcttttcc cccatctttg     300 ccaaatctca atgtatcgtt cttaacccca cctcctgtaa ggggctttgc tatgcttcag      360
ctggttgtct cagcagctga agtgctgccc acctgtgtga gttgggtcca ggaaaccatg      420
tctgcccttc tgataaggga agatgaatct agagctgggt gaagatctaa attttaacca      480
aacccctggg cccaggaaaa taacaattga aaatgtacaa ggcagtgttt tcaatattaa      540
acttccccaa ggaaagcaca aactagtctt tttggaaagg gagaaaggat taagccacac      600
agtattagtc tttgaagcag tactggtctc taggggctgg tgccaaaatg gagtcccata      660
gtagttacac tcgatggcct catgtactat atactgtgcc gaattgtatt aaacagtggt      720
ggggagttac tgggataaga acttgtctaa aagtttacaa accaaaacag atctgttagg      780
ttggtgcaaa agtaagtttt tgccatactt aatgtattgc cattaagtat ggcaaaaacc      840
acaattactt ttacaccaac ctatgtattt aagaatgttt ggtttgccag attccaaatg      900
aggtcttcag tgcagcaaag cccaaaaggt gtagactcag ttatgcaatt ataaggttaa      960
ggcgtagaag aaagctgctg ctaggttttt gttgcatttt acttgactgc tctgctgttt     1020
ttcttgtctc tcatgtttgg ttagctatga cttgagcatc ttggtaactg acaaaggtct     1080
tccttggggg acttgaacat cttggtaaat gacaggtctc cttggaggac tccagcagta     1140
tcttgtttaa acgactgaaa ggactattaa ggttgttgaa ttgtgttaat tggaactcat     1200
tgaggaaatg cgacattgat cctcctctta ttccacagtg tgttttctga tcatataaag     1260
aaggttccga accatccatc cccctcagag tttattcccc tggtaagctg taattgcata     1320
```

-continued

```
tccagtttaa actggactgg gactgcatgt tggtgaggat cggcaggggt tttccccctt    1380
ttcgaaagat gaaatagatt cttgagcact ggttgcagaa gccaaaatag ttcaaatagc    1440
tttgcataac cattgggttc tgcttctgat tcaggtgctg ggcatcatgt cctccctatt    1500
cttctcttct tggaaaccca gcctatctca taaatacctg cttccggcca cccatccaac    1560
ctccctgctc ctttcaacac aaatcttgga tattgccaaa ggaagccatt cagcagctgc    1620
tggggttttt catcccctg acatgcatac atttgctctg ggagaagtgt cttccctctg     1680
accctggtcc ccagctccgt ctgtgcttaa ttgctcttac ctgttgcact aatgaatatg    1740
actaggtttt aaaggggaa tgtgaagcaa taggcacatg gggcttggat gaattggtcc    1800
cacagatata ccctgcctta agccgctgag gtgatgagtc cactgctcat gtgaccctcc    1860
acctttgtgg atccctcttg gtttgtgacc agtgtgtctg tttgttgagg ttgtacaaac    1920
ttgacaaaag ttaatacttt tgtttgtatt ttctgcactg ttgcactctc caaatggccc    1980
cttgagtatt tttattgact tgttacacac attttttgtct ttgatgtcta catttttttcc   2040 tttaatgttt tttatttgga aggttacctg ctgttggatt taataaattt gtttacttga   2100
aaaaaaaaaa aaaaaaaa                                                  2118
```

<210> SEQ ID NO 6
<211> LENGTH: 21
<212> TYPE: RNA
<213> ORGANISM: Artificial Sequence
<220> FEATURE:
<223> OTHER INFORMATION: Synthetic siRNA #1 SEAT 1(sense)
<220> FEATURE:
<221> NAME/KEY: misc_feature
<222> LOCATION: (20)..(21)
<223> OTHER INFORMATION: deoxynucleotide sequence

<400> SEQUENCE: 6
gagugagcag uaagucugut t                                              21

<210> SEQ ID NO 7
<211> LENGTH: 21
<212> TYPE: RNA
<213> ORGANISM: Artificial Sequence
<220> FEATURE:
<223> OTHER INFORMATION: Synthetic siRNA #1 SEAT 1(anti_sense)
<220> FEATURE:
<221> NAME/KEY: misc_feature
<222> LOCATION: (20)..(21)
<223> OTHER INFORMATION: deoxynucleotide sequence

<400> SEQUENCE: 7
acagacuuac ugcucacuct t                                              21

<210> SEQ ID NO 8
<211> LENGTH: 21
<212> TYPE: RNA
<213> ORGANISM: Artificial Sequence
<220> FEATURE:
<223> OTHER INFORMATION: Synthetic siRNA #2 SEAT 1(sense)
<220> FEATURE:
<221> NAME/KEY: misc_feature
<222> LOCATION: (20)..(21)
<223> OTHER INFORMATION: deoxynucleotide sequence

<400> SEQUENCE: 8
cuuuuuggaa agggagaaat t                                              21

<210> SEQ ID NO 9
<211> LENGTH: 21

```
<212> TYPE: RNA
<213> ORGANISM: Artificial Sequence
<220> FEATURE:
<223> OTHER INFORMATION: Synthetic siRNA #2 SEAT 1(anti-sense)
<220> FEATURE:
<221> NAME/KEY: misc_feature
<222> LOCATION: (20)..(21)
<223> OTHER INFORMATION: deoxynucleotide sequence

<400> SEQUENCE: 9
uuucucccuu uccaaaaagt t                                              21

<210> SEQ ID NO 10
<211> LENGTH: 22
<212> TYPE: RNA
<213> ORGANISM: Artificial Sequence
<220> FEATURE:
<223> OTHER INFORMATION: Synthetic siRNA #3 SEAT 1(sense)
<220> FEATURE:
<221> NAME/KEY: misc_feature
<222> LOCATION: (21)..(22)
<223> OTHER INFORMATION: deoxynucleotide sequence

<400> SEQUENCE: 10
gagggaaaug cgacauugau tt                                             22

<210> SEQ ID NO 11
<211> LENGTH: 21
<212> TYPE: RNA
<213> ORGANISM: Artificial Sequence
<220> FEATURE:
<223> OTHER INFORMATION: Synthetic siRNA #3 SEAT 1(anti_sense)
<220> FEATURE:
<221> NAME/KEY: misc_feature
<222> LOCATION: (20)..(21)
<223> OTHER INFORMATION: deoxynucleotide sequence

<400> SEQUENCE: 11
aucaaugucg cauuuccuct t                                              21

<210> SEQ ID NO 12
<211> LENGTH: 21
<212> TYPE: RNA
<213> ORGANISM: Artificial Sequence
<220> FEATURE:
<223> OTHER INFORMATION: Synthetic DCUN 1D3 siRNA #2(sense)
<220> FEATURE:
<221> NAME/KEY: misc_feature
<222> LOCATION: (20)..(21)
<223> OTHER INFORMATION: deoxynucleotide sequence

<400> SEQUENCE: 12
caguguguca ccaaguguat t                                              21

<210> SEQ ID NO 13
<211> LENGTH: 21
<212> TYPE: RNA
<213> ORGANISM: Artificial Sequence
<220> FEATURE:
<223> OTHER INFORMATION: Synthetic DCUN 1D3 siRNA #2(antisense)
<220> FEATURE:
<221> NAME/KEY: misc_feature
<222> LOCATION: (20)..(21)
<223> OTHER INFORMATION: deoxynucleotide sequence

<400> SEQUENCE: 13
uacacuuggu gacacacugt t                                              21

<210> SEQ ID NO 14
```

```
<211> LENGTH: 21
<212> TYPE: RNA
<213> ORGANISM: Artificial Sequence
<220> FEATURE:
<223> OTHER INFORMATION: Synthetic DCUN 1D3 siRNA #3(sense)
<220> FEATURE:
<221> NAME/KEY: misc_feature
<222> LOCATION: (20)..(21)
<223> OTHER INFORMATION: deoxynucleotide sequence

<400> SEQUENCE: 14
gucacugcau cgggaaauat t                                              21

<210> SEQ ID NO 15
<211> LENGTH: 21
<212> TYPE: RNA
<213> ORGANISM: Artificial Sequence
<220> FEATURE:
<223> OTHER INFORMATION: Synthetic DCUN 1D3 siRNA #3(antisense)
<220> FEATURE:
<221> NAME/KEY: misc_feature
<222> LOCATION: (20)..(21)
<223> OTHER INFORMATION: deoxynucleotide sequence

<400> SEQUENCE: 15
uauuucccga ugcagugact t                                              21

<210> SEQ ID NO 16
<211> LENGTH: 23
<212> TYPE: RNA
<213> ORGANISM: Homo sapiens

<400> SEQUENCE: 16
caaagugcuc auagugcagg uag                                            23
```